United States Patent [19]

Perumattam

[11] Patent Number: 5,519,043
[45] Date of Patent: * May 21, 1996

[54] FLUORENYL DERIVATIVES

[75] Inventor: John J. Perumattam, Baltimore, Md.

[73] Assignee: Scios Nova Inc., Mountain View, Calif.

[ * ] Notice: The portion of the term of this patent subsequent to Dec. 5, 2012, has been disclaimed.

[21] Appl. No.: 56,907

[22] Filed: May 5, 1993

Related U.S. Application Data

[63] Continuation-in-part of Ser. No. 985,926, Dec. 4, 1992, which is a continuation-in-part of Ser. No. 805,639, Dec. 12, 1991, abandoned.

[51] Int. Cl.$^6$ .................. C07D 257/04; C07D 333; C07D 08; C07D 229; C07D 42; A61K 31/245; A61K 31/41

[52] U.S. Cl. .................. 514/381; 514/480; 514/567; 558/240; 562/433; 548/251; 548/253

[58] Field of Search .................. 514/381; 548/253, 548/251

[56] References Cited

U.S. PATENT DOCUMENTS

| | | | |
|---|---|---|---|
| 2,877,269 | 3/1959 | Campen et al. | 260/564 |
| 3,801,633 | 4/1974 | Toyoshima et al. | 260/518 |
| 3,835,175 | 9/1974 | Carpino et al. | 260/463 |
| 3,845,097 | 10/1974 | Toyoshima et al. | 260/471 |
| 3,906,031 | 9/1975 | Carpino et al. | 260/471 |
| 3,919,291 | 11/1975 | Toyoshima et al. | 260/482 |
| 5,079,260 | 1/1990 | Weitzberg et al. | 514/532 |

OTHER PUBLICATIONS

Rosenthale et al., "Immunopharmacologic Effects of Cycloleucine," *Journal of Pharmacology and Experimental Therapeutics*, vol. 180, No. 2, pp. 510–513 (1972).

Ludwig et al., "MER–27, a Suppressant of Non–Bacterial Pneumonia in Mice," *Proc. Soc. Exp. Biol. Med.*, vol. 100, pp. 495–497 (1959).

Carpino, "The 9–Fluorenylmethyloxycarbonyl Family of Base–Sensitive Amino–Protecting Groups," *Accounts of Chemical Research*, vol. 20, pp. 401–407 (1987).

Burch et al., "N–(Fluorenyl–9–methoxycarbonyl) amino acids, a class of antiinflammatory agents with a different mechanism of action," *Proc. Natl. Acad. Sci. USA*, vol. 88, pp. 355–359, Jan. 1991.

*Primary Examiner*—David B. Springer
*Attorney, Agent, or Firm*—Nath & Associates; Gary M. Nath

[57] ABSTRACT

The compound having the formula:

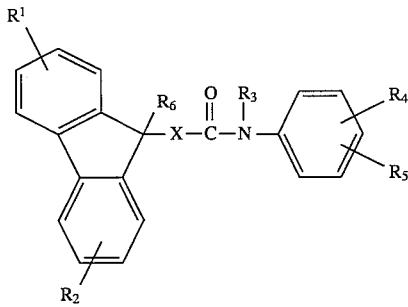

and a method of treating an inflammatory condition comprising administering to an animal in need of such treatment an effective amount of at least one compound represented by the formula.

25 Claims, No Drawings

FLUORENYL DERIVATIVES

RELATED APPLICATIONS

This application is a continuation-in-part application of U.S. application Ser. No. 07/985,926, filed Dec. 4, 1992, U.S. Pat. No. 5,472,973, which is a continuation-in part application of U.S. application Ser. No. 07/805,639 filed Dec. 12, 1991, now abandoned, the entire contents Of both applications are hereby incorporated by reference.

BACKGROUND OF THE INVENTION

1. Field of the Invention

This invention relates to novel fluorenyl derivative compounds, and more particularity to novel fluorenyl derivatives and pharmaceutical compositions suitable as anti-inflammatory agents.

2. Description of the Prior Art

The treatment of inflammatory conditions, such as atopic dermatitis, contact dermatitis, psoriasis, rheumatoid arthritis, glomerulonephritis, osteoarthritis, lupus erythematosus, scleroderma, asthma and irritable bowel disease has in the past, involved the use of agents such as aspirin-like nonsteroidal anti-inflammatory agents, glucocorticoids, methotrexate and cyclophosphamide. Unfortunately these agents generally produce unwanted side effects.

Nonsteroidal anti-inflammatory drugs (NSAIDs), while reducing inflammatory symptoms, do not prevent progression of disease and have serious side effects, including gastric ulceration. Glucocorticosteroids provide dramatic relief in some diseases but with systemic side effects, which often preclude chronic use at efficacious doses. Furthermore, certain cytotoxic agents can provide substantial relief but elicit major toxicity.

In contrast, methotrexate has been associated with patient death, cyclophosphamide has carcinogenic liability. Thus, new agents for treating inflammatory conditions that are free of these adverse side effects are needed.

Burch et al. in "N-(Fluorenyl-9-methoxycarbonyl) amino acids, a class of anti-inflammatory agents with a different mechanism of action", *Proc. Natl. Acad. Sci. USA* Vol. 88, pp. 355–359, January, 1991 discloses several members of a series of (N-fluorenyl-9-methoxycarbonyl) amino acids as possessing a broad spectrum of anti-inflammatory activity. The compounds are disclosed as being active against oxazolone dermatitis in mice and adjuvant arthritis in rat models in which activated T-lymphocytes are implicated. Burch et al. found that the compounds also inhibited T-lymphocyte activation in vitro, assessed by using the mixed lymphocyte reaction and that the compounds inhibited the reversed passive Arthus reaction in rats and arachidonic acid-induced dermatitis in mice models in which leukocyte infiltration is responsible for the inflammatory reaction.

SUMMARY OF THE INVENTION

The present invention relates to the formation of new fluorenyl compounds and more particularly to fluorenyl derivatives of various aminobenzoic acids. Applicants have unexpectedly discovered that the present compounds function as anti-inflammatory agents which do not act by inhibiting lipid metabolic enzymes. These materials are not steroids nor do they appear to increase the circulating levels of endogenous glucocorticoids. They do, however, appear to block or inhibit neutrophil and/or lymphocyte recruitment or migration into inflammatory lesions and may even inhibit T-cell activation. For this reason, the compounds of the invention can be useful in treating or preventing other disease states where it is desirable to inhibit neutrophil and/or lymphocyte recruitment or migration.

In a preferred aspect of the invention the compounds of the invention have the formula:

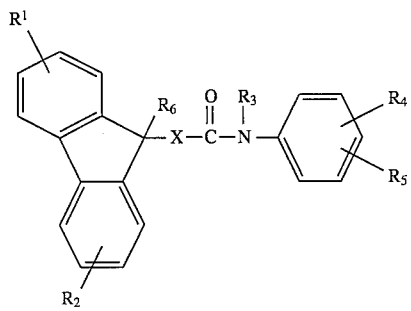

wherein

X is selected from the group consisting of $(CH_2)_n$, $(CH_2)_n O$ wherein n is 3 to 11, and $(CH_2)_{M-1} S$ wherein m is 1 to 11 and wherein the chains are straight or branched chains;

$R_1$ and $R_2$ are independently selected from the group consisting of hydrogen, $C_1$ to $C_6$ straight or branched chain lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ straight or branched chain lower alkyl groups;

$R_4$ is selected from the group consisting of nitro, hydroxyl, $-CO_2H$, $-NHSO_2R_7$, wherein $R_7$ is methyl, or trifluoromethyl; $-CONHSO_2R_8$, wherein $R_8$ is methyl, trifluoromethyl, or phenyl; 1-H-tetrazol-5-yl, $-(CH_2)_n COOH$ wherein n is 1, 2 or 3, and $-CO_2R_9$, wherein $R_9$ is $C_1$ to $C_6$ straight or branched chain lower alkyl, aryl or 1-H-tetrazol-5-yl;

$R_5$ is selected from the group consisting of hydrogen, $C_1$ to $C_6$ straight or branched chain lower alkyl, halogen, hydroxyl, and methoxy group; and $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic with hydrocarbo groups thereof.

Another aspect of the invention includes a method of treating an inflammatory condition comprising administering to an animal in need of such treatment an amount of at least one compound represented by the formula:

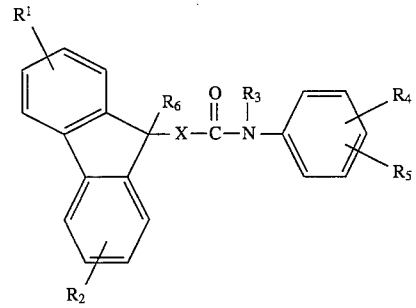

wherein:

X is selected from the group consisting of $(CH_2)_n$, $(CH_2)_n O$ wherein n is 3 to 11, and $(CH_2)_{m-1} S$ wherein m is 1 to 11 and wherein the chains are straight or branched chain;

$R_1$ and $R_2$ are independently selected from the group consisting of hydrogen, $C_1$ to $C_6$ straight or branched chain lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ straight or branched chain lower alkyl group.

$R_4$ is selected from the group consisting of nitro, hydroxyl, —$CO_2H$, —$NHSO_2R_7$, wherein $R_7$ is methyl, or trifluoromethyl; —$CONHSO_2R_7$, wherein $R_7$ is methyl, trifluoromethyl, or phenyl; 1H-tetrazol-5-yl,-$(CH_2)_n$ COOH wherein n is 1, 2 or 3, and —$CO_2R_9$, wherein $R_9$ is $C_1$ to $C_6$ straight or branched chain lower alkyl, aryl or 1H-tetrazolyl-5-yl;

$R_5$ is selected from the group consisting of hydrogen, $C_1$ to $C_6$ straight or branched chain lower alkyl, halogen, hydroxyl, and a methoxy group; and $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic with hydrocarbo groups thereof, or pharmaceutically acceptable salt thereof, sufficient to reduce or eliminate said inflammatory condition.

In another aspect of the invention the novel compounds are prepared as pharmaceutical compositions useful as anti-inflammatory agents. Such agents may be administered in many ways, such as topically, rectally, parenterally and orally.

DESCRIPTION OF THE PREFERRED EMBODIMENTS

The novel compounds of the invention have the formula:

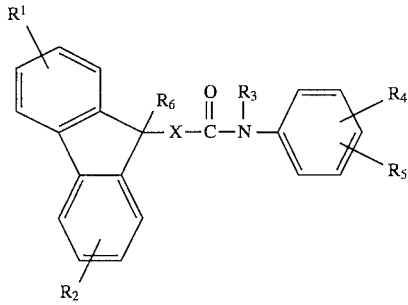

wherein

X is selected from the group consisting of $(CH_2)_n$, $(CH_2)_n$ O wherein n is 3 to 11, and $(CH_2)_{m-1}$ S wherein m is 1 to 11 and wherein the chains are straight or branched chains;

$R_1$ and $R_2$ are independently selected from the group consisting of hydrogen, $C_1$ to $C_6$ straight or branched chain lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ straight or branched chain lower alkyl group;

$R_4$ is selected from the group consisting of nitro, hydroxyl, —$CO_2H$, —$NHSO_2R_7$, wherein $R_7$ is methyl, or trifluoromethyl; —$CONHSO_2R_8$, wherein $R_8$ is methyl, trifluoromethyl, or phenyl; 1H-tetrazol-5-yl, —$(CH_2)_n$ COOH wherein n is 1, 2 or 3, and —$CO_2R_9$, wherein $R_9$ is $C_1$ to $C_6$ straight or branched chain lower alkyl, aryl or 1H-tetrazol-5-yl;

$R_5$ is selected from the group consisting of hydrogen, $C_1$ to $C_6$ straight or branched chain lower alkyl, halogen, hydroxyl, and a methoxy group; and $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic with hydrocarbo groups thereof.

In a preferred feature of the invention, X is selected from the group consisting of propyleneoxy, butyleneoxy, propylene, and thioethylene. Preferably $R_1$ and $R_2$ are independently selected from the group consisting of hydrogen, chlorine, bromine, and mixtures thereof. Alternatively, $R_1$ and $R_2$ are selected from the group consisting of 2,7-dimethyl, 2-7-diethyl, 2,7-di-t-butyl, 2,7-dibromo, and 2,7-dichloro. Preferably, $R_4$ is selected from the group consisting of -2—$CO_2H$, —3—$CO_2H$, -4—$CO_2H$, and -4—$CH_2CO_2H$ and $R_3$ is preferably selected from the group consisting of hydrogen, a hydroxyl group, and a methyl group.

Exemplary compounds of the invention may be selected from the group consisting of:

(4-[3-(9H-Fluoren-9-yl) propoxycarbonyl]aminobenzoic acid);

(4-[4-(9H-Fluoren-9-yl)butoxycarbonylamino]benzoic acid);

(4-[9H-Fluoren-9-yl)]butyric acid-4-carboxyanilide);

(N-[2-(9H-Fluoren-9-yl)ethylthioxycarbonyl]-4-aminobenzoic acid);

(N-[9H-(2,7-Dichlorofluoren-9-ylthioethoxycarbonyl))]-4-aminobenzoic acid); and (N-[9H-(2,7-dibromofluoren-9-ylthioxycarbonyl))]-4-aminobenzoic acid).

The terms used herein are used in their conventional manner, for example, "alkyl" is a straight or branched chain paraffinic hydrocarbon group which may be derived from an alkane by dropping at least one hydrogen from the formula, including methyl, ethyl, propyl, isopropyl, butyl, isobutyl, and so forth; "halogen" includes bromo, fluoro, chloro and iodo; "aryl" is an aromatic ring compound such as benzene, phenyl, naphthyl and substituted forms thereof; "aralkyl" is an aryl being attached through an alkyl chain, straight or branched, of from one through six carbons, and so forth; "alicyclic" is an organic compound characterized by a closed ring structure and include cycloparaffins, cycloolefins and cycloacetylenes.

The present inventive subject matter also entails a method of treating an inflammatory condition comprising administering to an animal in need of such treatment an amount of at least one compound represented by the following formula:

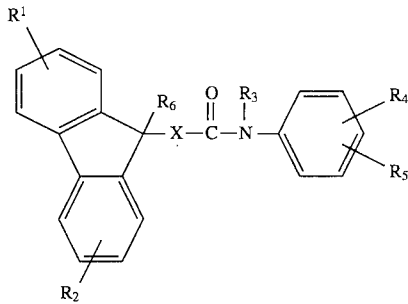

wherein

X is selected from the group consisting of $(CH_2)_n$, $(CH_2)_n$ O wherein n is 3 to 11, and $(CH_2)_{m-1}$ S wherein m is 1 to 11 and wherein the chains are straight or branched chain;

$R_1$ and $R_2$ are independently selected from the group consisting of hydrogen, $C_1$ to $C_6$ straight or branched chain lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ straight or branched chain lower alkyl group.

$R_4$ is selected from the group consisting of nitro, hydroxyl, —$CO_2H$, —$NHSO_2R_7$, wherein $R_7$ is methyl, or trifluoromethyl; —$CONHSO_2R_7$, wherein $R_7$ is methyl, trifluoromethyl, or phenyl; 1-H-tetrazolyl-5-yl,—$(CH_2)_n$ COOH wherein n is 1, 2 or 3, and —$CO_2R_9$, wherein $R_9$ is $C_1$ to $C_6$ straight or branched chain lower alkyl, aryl or 1H-tetrazol-5-yl;

$R_5$ is selected from the group consisting of hydrogen, $C_1$ to $C_6$ straight or branched chain lower alkyl, halogen, hydroxyl, and a methoxy group; and $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic hydrocarbo groups thereof, as well as pharmaceutical compositions containing the same.

The preparation of compounds for administration in pharmaceutical preparations may be accomplished in a variety of well known methods known to those skilled in the art of synthetic organic chemistry. Appropriate pharmaceutically acceptable salts within the scope of the invention are those derived from mineral acids such as hydrochloric acid, phosphoric acid, nitric acid and sulfuric acid; and organic acids such as tartaric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skill in the art. Merely for purposes of illustration, the class may be said to include mono-, di- and trialkylamines, such as methylamine, dimethylamine, and triethylamine; mono-, di- or trihydroxyalkylamines such as mono-, di-, and triethanolamine; amino acids such as arginine, lysine; guanidine; N-methyl-glucosamine; n-methylglucamine; L-glutamine-N-methylpiperazine; morphonline; ethylenediamine; N-benzylphenethylamine; tris(hydroxymethyl)aminomethane; and the like. (See for example, "Pharmaceutical Salts," J. Pharm. Sci. (1977) 66(1): 1–19.)

The compounds can be incorporated into convenient pharmaceutical dosage forms such as capsules, tablets, or injectable preparations. Solid or liquid pharmaceutical carriers can be employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, along or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques well known to a pharmaceutical chemist involving mixing, granulating, and compressing when necessary, for tablet forms, or mixing, filling, and dissolving the ingredients, as appropriate, to give the desired oral or parenteral products.

In parenteral administration (i.p.) of the novel compounds and compositions of the invention, they may be formulated in aqueous injection solutions which may contain antioxidants, buffers, bacteriostats, and so forth. Extemporaneous injection solutions may be prepared form sterile pills, granules or tablets which may contain diluents, dispersing and surface active agents, binders and lubricants.

In the case of oral administration, fine powders or granules of the compound may be formulated with diluents as well as dispersing and surface active agents. They may also be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the pharmaceutical art.

Preferably, the pharmaceutical compositions of the invention include the active ingredient in a quantity selected from 5 mg to 1000 mg, advantageously, from about 10 mg to 500 mg, per dosage unit, depending on the route of administration. Appropriate concentrations and dosage unit sizes can be readily determined by one of ordinary skill in the art.

As indicated above, the pharmaceutical compositions of the invention can be present in dosage unit form. For example, the composition can take the form of a tablet (preferably enteric coated), capsule, powder, troche, lozenge, inhalant, syrup, emulsion, gel, ointment, cream, lotion, transdermal patch, suppository, sterile injectable liquid as well as a liquid suspension or solution.

The method of treating an inflammatory condition according to this invention comprises administering to a subject in need of such treatment an effective amount of at least one of the novel compounds sufficient to produce an anti-inflammatory effect. The inventive compounds can be administered orally, nasally, topically, transdermally, parenterally or rectally, as may be required to effect the desired anti-inflammatory effect.

The active ingredient will normally be administered in a daily dosage regimen selected from about 10 mg to 1 g, most preferably from about 20 mg to about 500 mg. Advantageously, between one time per day to one time per week. The frequency of administration and the amount of active ingredient to be administered to effect treatment of a particular inflammatory condition can readily be determined by one skilled in the art. For inflammatory conditions of the lungs, an aerosol dispensing system wherein the active medicament is incorporated with an inert propellant in an aerosol container is of particular applicability. Such an aerosol system will deliver a metered dose of about 100 mcg to about 650 mcg, administered once or twice at a time as needed.

The novel compounds described herein may be prepared by methods well known in the art and as exemplified below. For example, details of general synthetic procedures involve the following reactions.

GENERAL METHODS OF PREPARATION

The compounds of Examples can be prepared according to the scheme as outlined below (Scheme 1). The fluorene- 9-methanol is converted into the corresponding chloroformate using phosgene and is then coupled with p-aminobenzoic acid.

Scheme 1

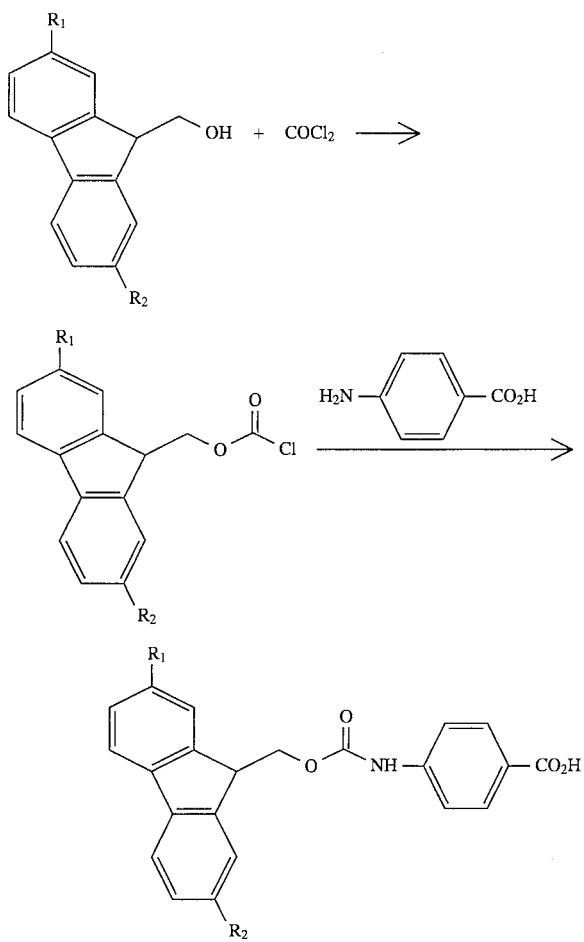

An alternative scheme would involve treating the fluorene anion with ethylene oxide to generate fluorene-9-ethanol which is converted to chloroformate using phosgene, then coupled with aminobenzoic acids.

Scheme 2

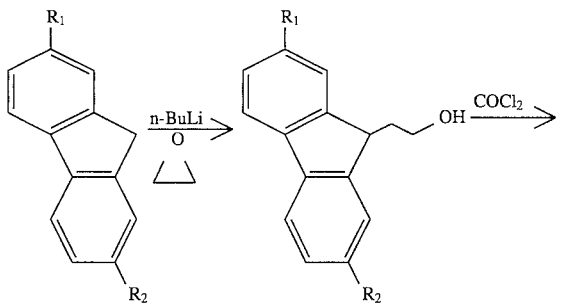

Scheme 2 —continued

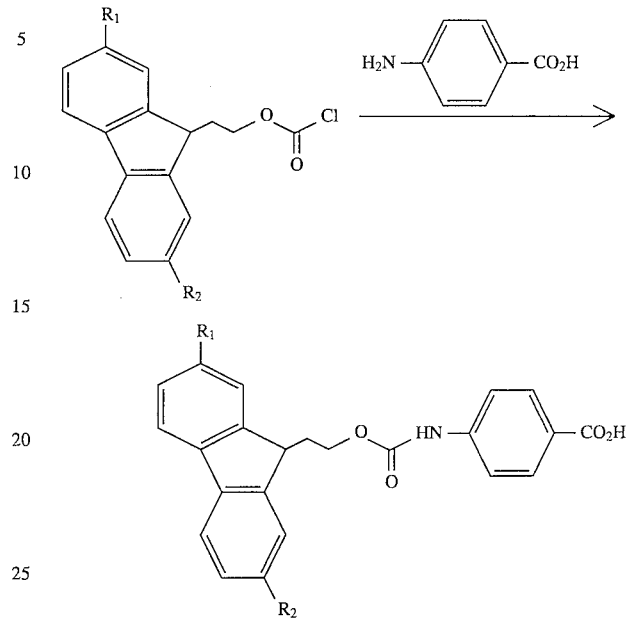

A third scheme (Scheme 3) for preparing the compounds of the invention involves treating the fluorene anion with 2-(2-bromoethyl)-1,3-dioxalane and then oxidizing the product using Jone's reagent to provide the acid. Thionyl chloride treatment of the acid gives the acid chloride which can then be coupled with aminobenzoic acids.

Scheme 3

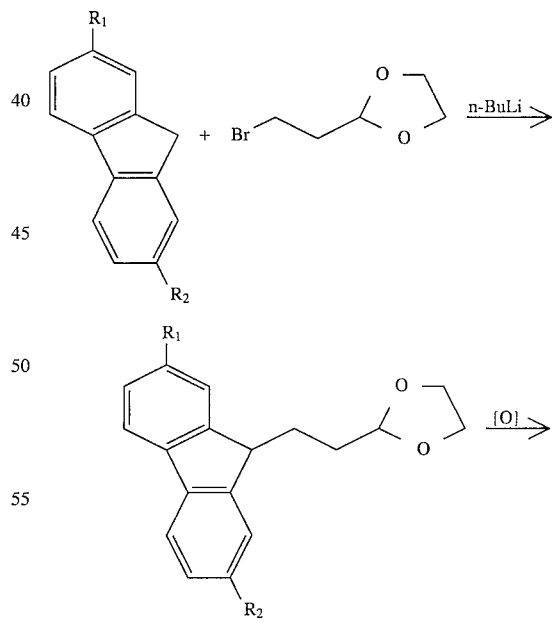

-continued
Scheme 3

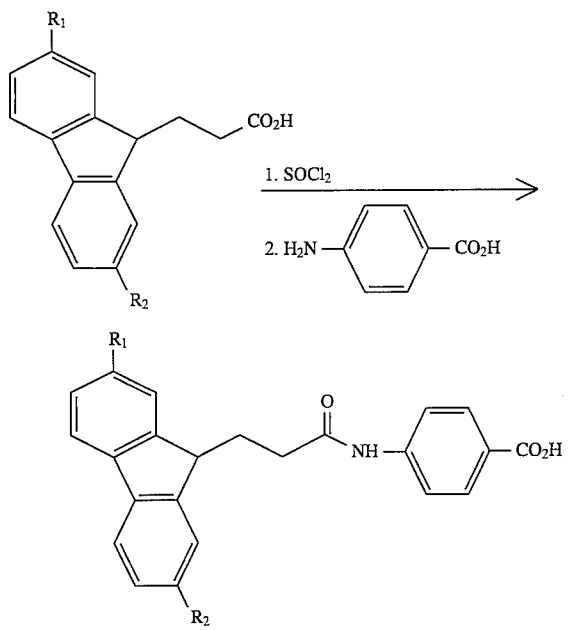

The activity of the present compounds as anti-inflammatory agents can be demonstrated in animals, such as mice, for example, by measuring the ability of the compound to inhibit edema caused by a variety of inflammatory agents that are generally accepted as producing irritation by differing mechanisms. Such inflammatory agents typically include oxazolone, and the like. The reverse passive Arthus test offers another measure of the compound's utility in preventing an inflammatory response (Chang et al. Eur. J. Phar. 69:155–164 (1981)).

Test compounds are typically administered intraperitoneally or orally. For intraperitoneal administration, the test compound can be given in dimethyl sulfoxide or in 0.5% methylcellulose 30 minutes prior to administration of the irritant. For oral administration, the test compound can be compounded into tablet or capsule form as well as dissolved in, for example, water or ethanol and swallowed prior to application of the irritant. Results can be expressed as the percent decrease in swelling in the compound-treated animals as compared to control animals that receive only the irritant.

It is noteworthy that currently available non-steroidal anti-inflammatory agents operate by a single mechanism (cyclo-oxygenase inhibitors), thus, they are highly active in a single assay (steroids are usually active in most, if not all, screens but have side effects that prohibit their widespread use). The compounds are highly active in almost all of the inflammatory screens and are also highly active in the reverse passive Arthus assay and in adjuvant arthritis, which are considered to be predictive of activity against human arthritis. That is, the present compounds have the steroid-like spectrum of activity but lack steroid-like toxicity.

The following non-limiting Examples, which are illustrative of the compounds suitable for use in the methods and compositions of the present invention, demonstrate the activity of these compounds as well as processes for their preparation.

Examples 1 to 6 demonstrates the formation of compounds having the general structure:

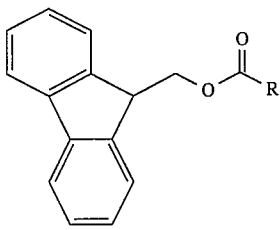

EXAMPLE 1

N-[9-H-(Fluorenyl-9-methoxycarbonyl)]anthranilic acid

To a clear solution containing 500 mg (3.26 mmol) of anthranilic acid and 450 mg (3.26 mmol) of potassium carbonate in 10 ml of water was added 765 mg (2.96 mmol) of fluorenylmethoxycarbonyl chloride in 10 ml of dioxane. The mixture was stirred at room temperature (22° C.) for 2.5 hours. Evaporation of the solvent gave an oil which was dissolved in water and acidified with 10% HCl whereupon a white solid separated. This was collected by filtration and dried. Recrystallization from 10% ethyl and acetate/hexane mixture provides a white solid (450 mg, 45%, mp 212°–214°. IR (KBr) 1738, 1668, 1591, 1527, 1450, 1262, 1213, 1054, 758 CM$^{-1}$; $^1$H NMR (DMSO, 300 MHz) 4.28(t, 1H, J=8.2 Hz) , 4.39 (d, 2H, J=7.2 Hz), 7.02 (t, 1H, J=7.6 Hz), 7.63(d, 1H, J=7.6 Hz), 7.82(d, 2H, J=7.6 Hz) 7.95(d, 1H, J=7.6 Hz), 8.17 (t, 1H, J=7.6 Hz), 11.17 (br, 1H), anal. calcd for $C_{22}H_{17}NO_4$: C, 73.53; H, 4.77; N, 3.90. Found C, 7.27; H, 4.82; N, 3.83.

EXAMPLE 2

N-[9H-Fluoren-9-ylmethoxy)carbonyl]-4-aminosalicylic acid

To a solution containing 1.0 g(6.5 mmol) of 4-aminosalicylic acid, 898 mg(6.5 mmol) of $K_2CO_3$ in 15 ml of dioxane and 5 ml of water was added 9-fluorenylmethyl chloroformate in 5 ml of dioxane. The reaction mixture was stirred for 2 hours at room temperature (22° C.) and the dioxane evaporated. The residue was diluted with water and extracted with ethyl acetate. The basic aqueous solution was then acidified with 10% HCl, the separated solids were collected by filtration and dried (1.85 g, 75%), mp 234°–235° C. (subl.). IR (KBr) 3342, 3016, 1715, 1643, 1594, 1519, 1450, 1229, 1198, 1110, 1056 cm$^{-1}$. NMR (300 MHz, DMSO-$d_6$)∂ 4.21 (t, 1H, J=6.6 Hz), 4.41 (d, 2H, J=6.6 Hz), 6.81–7.82 (m, 12H) , 9.7 (s, 1H) . Anal. Calcd for $C_{22}H_{17}NO_5$: C, 70.39; H, 4.56; N, 3.73. Found: C, 70.24; H, 4.59; N, 3.67.

EXAMPLE 3

N-[9H-(Fluorenyl-9-methoxycarbonyl)]-4-aminophenylacetic acid

To a solution of 9-fluorenyl methylchloroformate (2.0 g, 8 mmol) to 10 ml of dioxane was added dropwise with stirring a solution of 4-aminophenylacetic acid (1.28 g, 8.4 mmol) and potassium carbonate (1.16 g, 8.4 mmol) in 10 ml of water. A brown precipitate formed, and the solution was stirred for 2 hours, diluted with water, and acidified with 10% HCl. Concentration yielded a brown solid which was recrystallized two times for methanol, washed with hexane and dried to give white crystals of N-[9H-(Fluorenyl-9-methoxycarbonyl)]-4-aminophenylacetic acid (1.9 g 34% yield) mp 169° C. FTIR(KBr) 3319, 1702, 1599, 1529, 1450, 1419, 1316, 1244, 1229, 1108, 1092, 1051, 740 cm$^{-1}$. $^1$H NMR(300 MHz, DMSO) δ 3.45 (S, 2H), 4.28 (t, 1H, J=6.5 Hz), 4.44 (d, 2H, J=6.5 Hz), 7.12 (d, 2H, J=7.5 Hz), 7.35 (m, 7H), 7.72 (d, 2H, J=7.5 Hz), 7.88 (d, 2H, J=7.5 Hz), 9.64 (s, 1H). Anal. calcd for $C_{22}H_{19}NO_4 \cdot 0.5H_2O$: C, 72.24; h, 5.27; N, 3.66. Found: C, 72.41; H, 5.26; H, 3.91.

EXAMPLE 4

N-[9H-(Fluorenyl-9-methoxycarbonyl)]-N-methylanthranilic acid

To a solution of 9-fluorenylmethyl chloroformate (1.0 g, 3.9 mmol) in 10 ml of dioxane, was added dropwise with stirring a solution of N-methylanthranilic acid (0.60 g, 4.0 mmol) and potassium carbonate (0.55 g, 4.0 mmol) in 10 ml of water and 2 ml of dioxane. After 1 hour the solution was concentrated, suspended in 100 ml of water, and decanted from an oil. Acidification with 10% HCl yielded a tan solid of N-[9H-(Fluorenyl-9-methmoxycarbonyl)]-N-methylanthranilic acid, which was filtered off, washed with water, then hexane, and dried (0.6 g, 38%). mp 69°–72° C. FTIR(KBr) 3052, 1712, 1601, 1447, 1401, 1437, 1306, 1167, 1072, 1000, 768, 740, 712 cm$^{-1}$. $^1$H NMR (300 MHz, CDCl$_3$) δ 3.28 (m, 1H), 4.02 (m, 1H), 4.32 (m, 2H), 7.09–8.11 (m, 12H). Anal. calcd for $C_{23}H_{19}NO_4 \cdot 0.75\ H_2O$): C, 71.39; H, 5.34; N, 3.62. Found: C,71.23; H, 5.18; N, 3.64.

EXAMPLE 5

N-[9H-(Fluorenyl-9-methoxycarbonyl)]-4-aminophenyl-α-methylacetic acid

To a solution of 9-fluorenylmethyl chloroformate (1.68 g, 6.5 mmol) in 15 ml of dioxane was added dropwise with stirring a solution of 4-aminophenyl-α-methylacetic acid (1.0 g, 6.1 mmol) and potassium carbonate (2.07 g, 15 mmol) in 10 ml of water and 5 ml of dioxane. After 0.5 hours the solution was concentrated to remove the dioxane, suspended in 75 ml of water, and acidified with 10% HCl to yield a white precipitate which coagulated. The precipitate was removed, dried, broken into pieces, and washed with water, then hexane, and dried again. The solid was slurried in hot ethyl acetate, and filtered to give a white solid, 0.82 g (34%), mp 157°–160° C. FTIR 3334, 1704, 1596, 1529, 1452, 1419, 1308, 1234, 1095, 1409, 761, 748 cm$^{-1}$. $^1$H NMR (300 MHz, DMSO) δ 9.60 (s, 1H), 7.88 (d, 2H, J=7.0 Hz) , 7.43 (d, 2H, J=7.0 Hz) , 7.27–7.43 (m, 6H) , 7.13 (d, 2H, J=8.0 Hz), 4.93 (d, 2H, J=6.5 Hz), 4.27 (t, 1H, J=6.5 Hz), 3.42 (m, 1H), 1.24 (d, 3H, J=7.0 Hz). Anal. calcd for $C_{24}H_{21}NO_4 \cdot 1.25\ H_2O$: C, 70.31: H, 5.7: N, 3.41. Found: C, 70.66; H, 5.52:, N, 3.44.

EXAMPLE 6

N-(Fluorenyl-9-methoxycarbonyl)-N$^1$-acetylsulfanilamide

To a solution of 9-fluorenylmethyl chloroformate (1.0 g, 3.9 mmol) in 10 ml of dioxane was added dropwise with stirring a solution of N-acetylsulfanilamide sodium salt hydrate (0.92 g, 4.0 mmol) and potassium carbonate (0.62 g, 4.5 mmol) in 10 ml of water. After 2 hours the solution was concentrated, suspended in water, and acidified to pH 3 with 10% HCl to yield a white precipitate which was filtered off and dried to give 1.38 g (83%), mp 223°–227° C. FTIR (KBr) 3270, 1715, 1594, 1529, 1447, 1409, 1321, 1159, 1090, 1046 1002, 941, 869, 833, 740 cm$^{-1}$. $^1$HNMR (330 MHz, DMSO) δ 1.88 (s, 1H), 4.31 (t, 1H, J=7.5 Hz), 4.53 (d, 2H, J=6.5 Hz), 7.28–7.91 (m, 12H), 10.19 (s, 1H), 11.94 (s, 1H). Anal. calcd for $C_{23}H_{20}N_2O_5S$: C, 63.29; H, 4.62;, n, 6.42. Found: C, 63.42; H, 4.63; N, 6.33.

Examples 7 to 13 demonstrate the formation of compounds having the general structure:

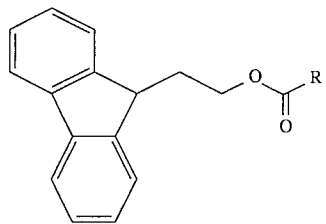

EXAMPLE 7

N-[9H-(Fluorenyl-9-ethoxycarbonyl)] amino-4-benzoic acid 2-(9-Fluorenyl) ethanol was prepared from a solution of fluorene (116.35 g, 0.7 mmol) in 800 ml of dry THF at −20° C. which was added n-Buli in hexane (0.7 mol) keeping the temperature below −10° C. To the clear solution was rapidly added 357 ml of 1.4M ethylene oxide in ether (0.5 mol) keeping the temperature below 5° C. The reaction mixture was stirred for 5 hours, then quenched with 50 ml of saturated ammonium chloride solution. The THF was removed at a rotary evaporator. The residue was partitioned between water and ethyl acetate. The organic layer was separated, dried with MgSO$_4$ and concentrated in vacuo until crystallization began. The solution was allowed to stand overnight and the crystals were collected and dried (mp 97° C.) (85.5 g, (81%)).

N-[9H-(Fluorenyl-9-ethoxycarbonyl)]amino-4-benzoic acid was prepared from a solution of 2-(9-fluorenyl) ethanol (1.5 g, 7.1 mmol) in 10 ml of toluene to which was added dropwise with stirring a solution of phosgene in toluene (12.4 ml, 1.93M). After 0.5 hours, the solution was put under vacuum to remove excess phosgene, and concentrated to yield 2-(9-fluorenyl)ethyl chloroformate. This was then dissolved in 10 ml of dioxane and add to a solution of 4-aminobenzoic acid (1.0 g, 7.3 mmol) in 15 ml water. After 5 hours, the dioxane was evaporated, the solution diluted with an equal amount of water, rendered basic with sodium carbonate solution, and filtered to remove insoluble materials. Acidification with 10% HCl yielded a white precipitate, which was filtered and dried. Crystallization from aqueous DMF gave a white solid (1.22 g, 46%), mp 202° C. IR(KBr) 3342, 2964, 2666, 2543, 2363, 1699, 1676, 1609, 1594, 1524, 1509, 1477, 1414, 1313, 1293, 1266, 1177, 1069, 1049, 938, 853, 768, 750, 735 cm$^{-1}$. $^1$H NMR (300 MHz, DMSO) δ 2.3(q, 2H, J=7.0), 400(t, 2H, J=7.0), 4.12(t, 1H, J=6.0), 7.29–7.88(m, 13H, 9.97(s, 1H). Anal. calcd for $C_{23}H_{19}NO_4 \cdot 0.25H_2O$: C, 73:10; H, 5.20; N, 3.71. Found: C, 73.32; H, 5.23; H, 3.70.

EXAMPLE 8

N-[9H-(2,7-Dimethylfluorenyl-9-ethoxycarbonyl)] amino-4-benzoic acid

This compound is prepared according to the procedure of Example 1 using 2-[9-(2,7-dimethylfluorenyl)] ethanol as

13 the starting material instead of 2-(9-fluorenyl) ethanol.

EXAMPLE 9

N-[9H-(2,7-Dichlorofluorenyl-9-ethoxycarbonyl) amino-4-benzoic acid

This compound is prepared according to Example 8 using 2-[9-(2,7-dichlorofluorenyl)] ethanol as the starting material.

EXAMPLE 10

N-[9H-(Fluorenyl-9-ethoxycarbonyl)amino-3-benzoic acid

This compound is prepared according to Example 1 using 3-aminobenzoic acid instead of 4-aminobenzoic acid.

EXAMPLE 11

N-[9H-(Fluorenyl-9-ethoxycarbonyl)anthranilic acid

A phosgene solution (12.4 ml of a 1.93M solution in toluene) was added dropwise with stirring to a solution of 2-(9-fluorenyl)ethanol (1.26 g, 6 mmol). After 0.5 hours the solution was put under vacuum to remove the phosgene, and concentrated to give 2-(9-fluorenyl)ethyl chloroformate (1.64 g, 6 mmol). This was dissolved in 10 ml dioxane, and to it added dropwise a solution of anthranilic acid (0.85 g, 6.2 mmol) and potassium carbonate (0.86 g, 6.2 mmol) in 15 ml water. After 3 hours, the dioxane was evaporated, and the solution diluted with an equal amount of water. Acidification with 10% HCl yielded a white precipitate which was washed with water and dried. (1.98 g, 88%), mp 177° C. IR(KBr) 3175, 1709, 1684, 1594, 1537, 1450, 1380, 1301, 1259, 1205, 1146, 1049, 753, 740 cm$^{-1}$. $^1$H NMR (300 MHz, CDCl$_3$) δ 2.46 (q, 2H, J=6.8), 4.14 (t, 3H, J=6.8), 7.10 (t, 1H, J=6.5), 8.46 (m, 13H), 10.13 (s, 1H). Anal. calcd for C$_{23}$H$_{19}$NO$_4$: C, 73.98; H, 5.13; N, 3.75. Found: C, 73.87; H, 5.19; N, 3.73.

EXAMPLE 12

N-[9H-(Fluorenyl-9-ethoxycarbonyl)]-4-aminosalicylic acid

To a solution of 2-(9-fluorenyl)ethanol 1.26 g, 6 mmol) in 10 ml of toluene and 4 ml of tetrahydrofuran (THF), was added dropwise with stirring phosgene (12.4 ml, 1.93M solution in toluene). The solution was stirred for 0.5 hours, then put under vacuum to remove the phosgene. Concentration yielded 2-(9-fluorenyl)ethyl chloroformate (6 mmol, 1.64 g).

To a solution of 4-aminosalicylic acid (0.95 g, 6.2 mmol) and potassium carbonate (0.82 g, 6.2 mmol) in 15 ml of water, was added dropwise with stirring a solution of 2-(9-fluorenyl)ethyl chloroformate (1.64 g, 6.0 mmol) in 10 ml of dioxane. The solution was concentrated after 2 hours, then diluted with water and made basic with 10% sodium carbonate. Acidification with 10% HCl yielded N-[9 H-(Fluorenyl-9-ethoxy carbonyl)]-4-aminosalicylic acid, which was filtered off and purified by reverse phase chromatography (C$_{18}$) using methanol/water, 6:4 as eluent to give 0.66 g (28%) of a solid, mp 230° C. FTIR(KBr) 3396, 3013, 1753, 1655, 1617, 1517, 1478, 1442, 1288, 1275, 1262, 1211, 1175, 1105, 1051, 1010, 959, 851, 786, 753, 735 cm$^{-1}$. $^1$H NMR (300 MHz, DMSO) δ 2.30 (q, 2H, J=3.5 Hz), 4.00 (t, 2H, J=3.5 Hz), 4.12 (t, 1H, J=3.5 Hz), 6.91–7.8 (m, 11H).

14

Anal. calcd for C$_{23}$H$_{19}$N$_5$O: C, 70.94; H, 4.92; N, 3.60. Found: C, 70.86; H, 4.97; N, 3.56.

EXAMPLE 13

N-[9H-(Fluorenyl-9-ethoxycarbonyl)]-4-aminophenylacetic acid 2-(9-Fluorenyl)ethyl chloroformate was prepared from a solution of 2-(9-fluorenyl)ethanol (1.26 g, 6.0 mmol) in 10 ml of toluene and 4 ml of tetrahydrofuran, which was added to 12 ml of phosgene solution (12.4 mol, [1.93M in toluene). The solution was stirred for 1 hour and put under vacuum to remove the phosgene. Concentration yielded 2-(9-fluorenyl)ethyl chloroformate (1.64 g, 6.0 mmol).

N-[9H-(Fluorenyl-9-ethoxycarbonyl)]-4-aminophenylacetic acid was prepared from a solution of 4-aminophenylacetic acid (0.94 g, 6.2 mmol) and potassiumcarbonate (0.86 g, 6.2 mmol) in 10 ml of water, which was added dropwise with stirring to a solution of 2-(9-fluorenyl)ethyl chloroformate (1.64 g, 6.0 mmol) in 10 ml of dioxane. After 4 hours the solution was concentrated, diluted with water and acidified with 10% HCl. A precipitate formed, and was purified by reverse phase chromatography, eluting with methanol/water, 6:4 to give N-[9H-(Fluorenyl-9-ethoxycarbonyl)-4-aminophenylacetic acid (0.90 g, 38%), mp 107° C. IR(KBr) 3314, 3041, 2980, 2933, 2365, 1697, 1604, 1532, 1447, 1475, 1414, 1239, 1077, 1056, 804, 758, 745, 673, 527 cm$^{-1}$. $^1$H NMR (300 MHz, DMSO): δ 9.55(s, 1H), 7.87(d, 2H, J=6.5 Hz), 7.62(d, 2H, J=6.5 Hz), 7.35(m, 6H), 7.10(d, 2H, J=8.3 Hz), 4.12(t, 1H, J=7.0 Hz), 3.98(t, 2H, J=7.0 Hz), 3.45(s, 1H), 2.28(q, 2H, J=7.0 Hz). Anal. calcd for C$_{24}$H$_{21}$NO$_4$0.25 H$_2$O: C, 73.54; H, 5.53; H, 3.57. Found: C, 73.89; H, 5.53; n, 3.60

Examples 14 and 15 demonstrate the formation of compounds having the general structure:

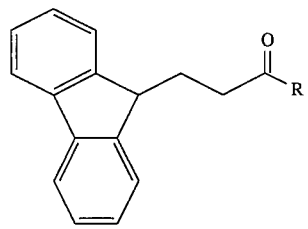

EXAMPLE 14

N-[3-(9-Fluorenyl)propionyl]anthranilic acid 2-(9-Fluorenyl)ethyl-1,3-dioxolane was prepared from a solution of fluorene (30.0 g, 180.5 mmol) in 400 ml of dry THF cooled in a −78° C. bath under argon, to which was added 100 ml of n-butyllithium (2.0M in cyclohexane) over 15 minutes After stirring for 0.5 hours at 78° C. 2-(2-bromoethyl)-1, 3-dioxolane (22.3 ml, 190 mmol) was added dropwise, and the resulting solution stirred at room temperature for 16 hours. Concentration in vacuo yielded an orange residue which was partitioned between ethyl acetate and saturated ammonium chloride. The organic layer was then washed with brine, dried with magnesium sulfate, and concentrated in vacuo to afford an orange oil. Flash chromatography on silica, hexane:ethyl acetate 20:1 to 1:1 yielded a yellow oil (36.38 g, 76%).

3-(9-Fluorenyl)propionic acid was prepared from 2-(9-fluorenyl) ethyl-1,3-dioxolane (50.0 g, 187 mmol) which was dissolved in 20 ml of acetone and 450 ml of Jones' reagent (64 g chromic acid and 64 ml of sulfuric acid in 400 ml of water). After the reaction was complete, the acetone was evaporated, the residue taken into ethyl acetate, washed with water, and organic layer extracted with 1N sodium hydroxide which was acidified with 10% HCl to yield a tan precipitate. FTIR 1954, 1913, 1707, 1429, 1316, 1257, 1208, 948, 933, 735 cm$^{-1}$. $^1$H NMR (300 MHz, DMSO-dis) δ 1.84 (t, 2H, J=7.5 Hz), 2.21 (m, 2H), 4.03 (t, 2H, J=5.5 Hz), 7.28–7.38 (m, 4H), 7.56 (d, 2H, J=7.0 Hz), 7.84 (d, 2H, J=7.0 Hz).

To prepare 3-(9-fluorenyl)propionic acid chloride, 3-(9-fluorenyl)propionic acid (1.0 g, 4.2 mmol) was refluxed in 5 ml of thionyl chloride for 1.5 hours. The solution was then concentrated to a brown oil, which solidified under high vacuum.

To prepare N-[3-(9-fluorenyl)propionyl]-anthranilic acid a solution of anthranilic acid (0.57 g, 4.2 mmol and 0.65 ml pyridine 8.4 mmol) in 15 ml of methylene chloride was added dropwise with stirring a solution of 3-(9-fluorenyl-)propionic acid chloride (1.10 g, 4.2 mmol) in 10 ml of methylene chloride. After 6 hours, the solution was then washed with 10% HCl, then brine, dried with magnesium sulfate, and concentrated to give 1.40 g (92%), of a white solid, mp 167°–172° C. FTIR (KBr) 3332, 1679, 1601, 1583, 1532, 1457, 1411, 1259, 1167 cm$^{-1}$. $^1$H NMR (300 MHz, DMSO) δ 2.02(t, 2H, J=7.0 Hz), 2.37 (m, 2H), 4.10 (t, 1H, J=6.5 Hz), 7.07–7.91 (m, 12H), 8.35 (d, 1H, J=8.0 Hz). Anal. calcd for $C_{23}H_{19}NO_3$: C, 77.29; H, 5.35; N, 3.92. Found: C, 77.16; H, 5.36; N, 3.84.

EXAMPLE 15

N-[3-(9-Fluorenyl)propionyl]-4-aminosalicylic acid

Preparation of N-[3-(9-Fluorenyl)propionyl]-4-aminosalicylic acid hydrate was performed as follows. 2-(9-Fluorenyl)propionic acid (1.0 g, 4.2 mmol) was refluxed in 5 ml of thionyl chloride for 1.5 hours and the excess thionyl chloride evaporated in vacuo. The residue was dissolved in 10 ml of methylene chloride and added dropwise to a suspension of 4-aminosalicylic acid (0.64, 4.2 mmol) and pyridine (0.65 ml 8.4 mmol) in 15 ml of methylene chloride. After 3 hours, the reaction was concentrated, taken into ethyl acetate, washed with 10% HCl, and the organic layer dried with magnesium sulfate and concentrated to a tan solid which was purified by reverse phase flash chromatography ($C_{18}$) eluting with methanol/water 50/50 then 70/30 to give a white solid, mp 225°–228° C. FTIR (KBr) 1643, 1511, 1450, 1367, 1257, 1167, 879, 830, 740, 671 cm$^{-1}$. $^1$H NMR (300 MHz, DMSO) δ 1.92 (t, 2H, J=7.5 Hz), 2.35 (m, 2H), 4.09 (t, 1H, J=5.0 Hz), 6.92 (dd, 1H, J=8.5 Hz), 7.24–7.39 (m, 8H), 7.61 (m, 2H), 7.86 (d, 2H, J=7.5 Hz) 9.94 (s, 1H). Anal. calcd for $C_{23}H_{19}NO_4 \cdot 0.25H_2O$: C, 73.09; H, 5.20; N, 3.71. Found: C, 73.19; H, 5.30; N, 3.80.

EXAMPLE 16

N-[9H-(Fluorenyl-9-ethoxycarbonyl)]-4-aminophenyltetrazole

To a solution of 9-fluorenyl ethanol (5.0 g, 23.8 mmol) and 190 mg (2.4 mmol) of pyridine in 50 ml of $CH_2Cl_2$ at 0° C. was added 3.5 g (11.8 mmol) of triphosgene. The mixture was stirred at 0° C. for 1 hour, then at room temperature for 3 hours. To this solution was added 2.8 g (23.78 mmol) of p-aminobenzonitrile in 15 ml of $CH_2Cl_2$. The mixture was stirred for 20 hours, washed with 10% $Na_2CO_3$, 10% HCl, dried with $MgSO_4$, and concentrated to afford a residue which was diluted with 10% ethyl acetate/hexane to obtain N-[9H-(fluorenyl-9-ethoxycarbonyl)]-4-aminobenzonitrile as a white solid, mp 161°–163° C. (6.0 g, 70%).

To a solution containing the above nitrile (5.85 g, 16.36 mmol) in 70 ml of N-methyl-2-pyrrolidinone was added 3.4 g (52.3 mmol) of sodium azide and 3.4 g (24.7 mmol) of triethylamine hydrochloride. The mixture was heated in a sealed tube at 130° C. for 3 hours, cooled, and 200 ml of water was added, acidified to pH=1 with 10% HCl (caution: possibility of hydrazonic acid formation) and extracted with ethyl acetate. The extract dried with $MgSO_4$, and concentrated to a brown liquid. This was diluted with ethyl acetate and the tetrazole was extracted with 10% NaOH. The basic solution was acidified to pH=2. The white solid was collected and dried. Recrystallization from MeOH provided 4.0 g (62%) of tetrazole was white powder, mp 238°–240° C. IR (KBr): 1702, 1604, 1542, 1511, 1434, 1339, 1244, 1095, 1054, 853, 745 cm$^{-1}$. $^1$NMR (300 MHz, DMSO-$d_6$) δ 2.32 (q, 2H, J=7.0 Hz), 4.02 (t, 2H, J=7.0 Hz) 4.13 (t, 1H, J=7.0 Hz), 7.31–7.93 (m, 12H), 9.98 (s, 1H). Anal. calcd for $C_{23}H_{19}N_5O_2$: C, 69.51; H, 4.82; N, 17.62. Found: C, 69.43; H, 4.87; N, 17.66.

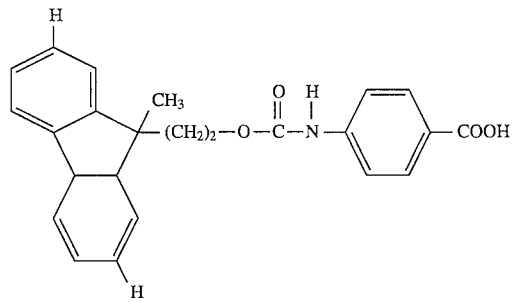

EXAMPLE 17

N-(2-[(9-methyl-9H-fluoren-9-yl]-ethoxycarbonyl-4-aminobenzoic acid a) 9-Methylfluorene. To a solution of fluorene (10.0 g, 60.0 mmol) in 100 mL of THF was added n-BuLi (66.6 mmol) at −78° C. This solution was then added to a chilled solution of iodomethane (15.04 g, 90.6 mmol) in 60 mL of THF. The temperature was kept at about −20° C. to maintain a clear solution. The mixture was allowed to warm to room temperature and then quenched with saturated aqueous $NH_4Cl$ and evaporated to a residue which was partitioned between ethyl acetate and water. The organic layer was washed with brine, dried with $MgSO_4$, filtered and evaporated to a solid. This solid was dissolved with hot pentane, stirred with decolorizing charcoal, filtered through a celite pad, and evaporated to get 10.0 g(92%) of 9-methyl fluorene was a white solid, mp 42°–43° C. FT-IR (KBr): 3065, 3039, 3016, 2962, 2926, 2864, 1478, 1445, 1309, 1023, 792 cm$^{-1}$. NMR (300 MHz, $CHCl_3$) δ 1.60–1.62(d, 3H, J=7.5 Hz), 3.93–3.97(q, 1H, J=7.5 Hz), 7.32–7.38 (m, 4H), 7.35–7.36 (d, 2H, J=8.0 Hz), 7.81–7.83(d, 2H, J=8.0 Hz).

b) 9-Methylfluorene-9-ethanol. To a solution of 9-methylfluorene (10.0 g, 55.5 mmol) in 100 mL of THF was added n-BuLi (61.0 mmol) at −10° C., then a solution of ethylene oxide (61.0 mmol) in THF was added in one portion. The reaction mixture was stirred at −20° C., then allowed to warm to room temperature, quenched-with NH₄Cl solution and evaporated to a residue. This was then partitioned between ethyl acetate and water, the organic layer was washed with brine, dried with MgSO₄ and evaporated to get the product which was purified by chromatography using 10% ethyl acetate/hexane mixture to provide a pure sample of 9-methylfluorene-9-ethanol, m.p. 84°–85° C.

c) N-{2-[(9-Methyl-9H-fluoren-9-yl]-ethoxycarbonyl-4-aminobenzoic acid. To a solution of 9-methylfluorene-9-ethanol (6.5 g, 28.9 mmol) in 60 mL of THF was added 18.6 Ml (35.9 mmol) of phosgene solution in toluene. Stirred for 3 hours, then excess phosgene was removed by passing argon and by trapping it in KOH solution. The material was evaporated to a residue which was then dissolved in 100 mL THF and added to a solution of p-aminobenzoic acid (7.9 g, (57.8 mmol) in 100 mL of THF. Concentrated to a slurry, then filtered, washed with 1N HCl solution, dried, mp 192°–193° C., FT-IR (KBr): 3467, 3250, 3165, 3039, 2992, 2869, 2666, 2553, 1707, 1679, 1604, 1522, 1458, 1419, 1355, 1311, 1291, 1237, 1216, 1180, 1054, 851, 735 cm⁻¹, NMR (300 MHz, DMSO-d₆); δ 1.87 (br, 1H, 1.48(S, 3H), 32.47 (t, 2H), 3.38 (t, 2H), 7.30–7.91 (m, 8H), 9.84 (s, 1H). Anal. Calcd for $C_{24}H_{21}NO_4$: C, 74.40; H, 5.46; N, 3.02. Found: C, 74.46; H, 5.48; N, 3.64.

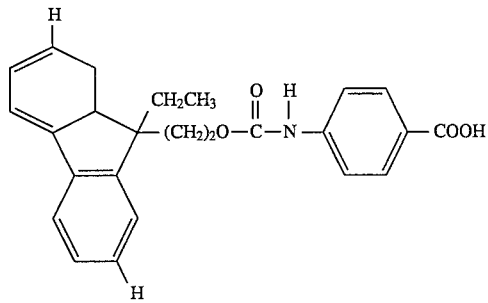

EXAMPLE 18

N-(2-[(9-Ethyl-9H-fluoren-9-yl]-ethoxycarbonyl-4-aminobenzoic acid

The procedure of Example 17 was repeated to form 9-ethylfluorene-9-ethanol as the product of steps a and b, giving 5.67 g ( 92.4%, m.p. 105°–1078° C.).

N-{2-[9-Ethyl-9H-fluoren-9-yl]-ethoxycarbonyl-4-aminobenzoic acid was prepared according to step c described above. FT-IR (KBr): 3397, 3322, 3065, 3008, 2957, 2931, 2898, 2875, 2669, 2546, 1710, 1676, 1610, 1594, 1440, 1417, 1314, 1288, 1229, 1178, 1067, 754 cm⁻¹. NMR (300 MHz, DNSO-d₆): 0.32 (t, 3H), 2.01 (q, 2H), 2.48 (t, 2H), 2.6 (br S, 1H), 3.52 (1:, 2H), 7.34 (m, 4H), 7.41 (m, 2H), 7.73 (d, 2H), 7.91 (d, 2H), 8.63 (br, 1H). Anal. Calcd for $C_{25}H_{23}NO_4$: C, 74.80; H, 5.77; N, 3.59. Found: C, 74.71; H, 3.77; N, 3.54.

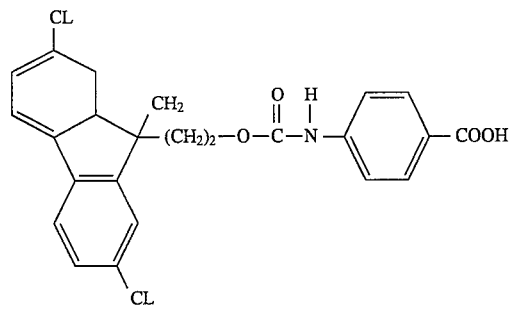

EXAMPLE 19

N-[9-methyl-(2,7-dichlorofluorenyl-9-ethoxycarbonyl)]-4-aminobenzoic acid.

a) 2,7-dichloro-9-methylfluorene.9-Methylfluorene (43.6 g, 0.24 mol) and N-chlorosuccinimide (64.5 g, 0.48 mol) were suspended in 25 mL of acetonitrile and cooled in an ice-water bath. Then 20 mL of concentrated HCl was added dropwise and the solution was stirred at room temperature overnight. The precipitate was filtered and dried. Recrystallization from EtOH and water gave 24 g (41%) of 2,7-dichloro-9-methylfluorene as white crystals, mp 110°–112° C. FT IR: 3425, 1450, 1407, 1273, 1167, 1070, 851,818 cm⁻¹; H¹ NMR (CDCl₃, 300 MHz) a 7.3–7.8 (m, 6H, 3.9–4.1 (q, 1H), 1.2–1.3 (d, 2H).

b) 2,7-Dichloro-9-methylfluorene-9-ethanol. To a solution of 2,7-dichloro-9-methylfluorene (2.1 g, 8.4 mmol) in 20 mL of THF was added 2.5M n-BuLi in hexane (3.36 mL, 8.4 mmol) at −78° C. and stirred for 0.5 hours under argon. To this solution 1.65M ethylene oxide in THF (7.27 mL, 12 mmol) was added rapidly and the solution was allowed to warm to room temperature slowly. Quenched with NH₄Cl solution, concentrated to a residue, then extracted with ethyl acetate. The organic layer was dried with MgSO₄ and concentrated under reduced pressure to a residue which upon silica gel column chromatographic purification using 20% ethylacetate/hexane provided 1.0 g(41%) of pure product as white solid: H¹ NMR (CDCl₃, 300 MHz) δ 7.3–8.7 (m, 6H), 3.0–3.1 (q, 2H), 2.2–2.3 (t, 2H), 1.4–1.5 (s, 3H).

c) N-[9-methyl-(2,7-dichlorofluorenyl-9-ethoxycarbonyl) ]-4-aminobenzoic acid. To a solution of 2,7-dichloro-9-methylfluorene-9-ethanol (2.98 g, 10.16 mmol) in 3 mL of dry THF was added 2 mL (10.36 mmol) of phosgene solution in toluene and stirred at room temperature for 2 hours. It was then concentrated at reduced pressure (properly trapping excess phosgene) and dissolved in 3 mL 1,4-dioxane. This was added to a dioxane/water (1:1) solution containing 4-aminobenzoic acid (1.67 g, 12.19 mmol) and potassium carbonate (1.68 g, 12.19 mmol ) and the reaction mixture was stirred overnight. Evaporated off the dioxane, the residue was dissolved in water and acidified to give white solids which was separated and dried, mp 215°–216° C.: IR 3402, 3312, 1687, 1597, 1538, 1417, 1237, 1175, 1067, 854, 812, 771 cm⁻¹; H¹ NMR (CDCl₃, 300 MHz) δ 12.6–12.8 (s, 1H), 7.4–8.0 (m, 10H), 3.3–3.5 (t, 2H), 2.4–2.6 (t, 2H), 1.4–1.5 (s, 3H). Anal. Calcd for $C_{24}H_{19}Cl_2O_4$: C, 63.17; H, 4.20; N, 3.07; Cl, 15.54. Found: C, 62.91; H, 4.27; N, 3.00; Cl, 15.44.

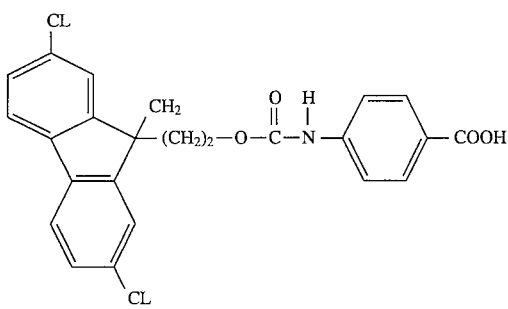

EXAMPLE 20

N-[9-ethyl-(2,7-dichlorofluorenyl-9-ethoxy carbonyl)]-4-aminobenzoic acid a) 2,7-Dichloro-9-ethylfluorene. To a solution of 2,7-dichlorofluorene (1.0 g, 4.3 mmol) in 3 mL of THF was added n-BuLi (2 mL, 5.0 mmol) at −78° C. under argon and the solution was stirred at −78° C. for 0.5 hours. A solution of $C_2H_5I$ (0.78 g, 5.0 mmol) in 1 mL of THF was poured into the solution and stirred at −78° for 15 min, quenched with $NH_4Cl$ solution, concentrated and extracted the residue with ethyl acetate, dried with $MgSO_4$ and evaporated to get the crude product which was purified by silica gel column chromatography using hexane as the eluent to obtain 1.35 g (74%) of 2,7-dichloro-9-ethylfluorene was a white solid, mp 80°–83° C.: IR: 3435, 1453, 1422, 1296, 1160, 1072, 885, 807 $cm^{-1}$. $H^1$ NMR ($CDCl_3$, 300MHz) δ 7.2–7.8 (m, 6H), 3.9–4.1 (t, 1H), 2.0–2.2 (m, 2H), 0.6–0.8 (t, 3H).

b) 2,7-Dichloro-9-ethylfluorene-9-ethanol. The compound was prepared according to step b of Example 19 to provide: $H^1$ NMR ($CDCl_3$, 300 MHz) d 7.2–7.6 (m, 6H), 2.9–3.1 (m, 2H), 2.2–2.3 (t, 2H), 1.9–2.1 (q, 2H), 0.2–0.3 (t, 3H).

c) The title compound was obtained according to step c) of Example 19 as a white solid having, mp 212°–213° C.: IR: 2355, 1702, 1687, 1607, 1527, 1417, 1216, 1175, 1072, 854, 812, 771 $cm^{-1}$. $H^1$ NMR ($CDCl_3$, 300 MHz) d 7.4–8.0 (m, 10H), 3.3–3.4 (t, 2H), 2.4–2.6 (t, 2H), 2.1–2.3 (q, 2H), 0.2–0.3 (s, 3H). Anal. Calcd for $C_{25}H_{21}C_2O_4$: C, 63.23; H, 4.56; N, 2.94; Cl, 15.07. Found: C, 63.20; H, 4.72; N, 2.93; Cl, 14.92.

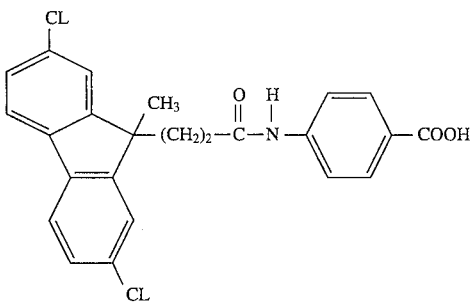

EXAMPLE 21

9-methyl-N-[3-(9-(2,7-dichlorofluorenyl))propionyl]-4-aminobenzoic acid a) and b) 2,7-Dichloro-9-methylfluorenyl-9-propionic acid. To a solution of 2,7-dichloro-9-methylfluorene (3.23 g, 12.96 mmol ) in 20 ml of THF was added n-BuLi (12.96 mmol) at −78° C. After 15 minutes, 2-(2-bromoethyl)-1,3-dioxalane (2.34 g, 12.96 mmol) was added dropwise and the solution was stirred at −78° C. for 2 hours, allowed to warm to room temperature and was further stirred for 2 hours. The mixture was quenched with $NH_4Cl$ solution, concentrated to residue, extracted with ethyl acetate. The organic layer was dried with $MgSO_4$ and evaporated to an oil which was subjected to flash silica gel chromatography to give 3.34 g (84%) of 2,7-dichloro-9-methylfluorenylethylacetal. The acetal was dissolved in 15 ml acetone, 24.43 mL (39 mmol) Jones' reagent was added dropwise and stirred at room temperature overnight. The reaction mixture was diluted with water and extracted with ethyl acetate. Silica gel column chromatographic purification using 20% ethyl acetate/hexane gave 1.43 g (34%) of 2,7-dichloro-methylfluorenyl-9-propionic acid as white crystal: $H^1$ NMR ($CDCl_3$, 300 MHz) δ 7.2–7.7 (m, 6H), 2.2–2.4 (m, 2H), 1.5–1.7 (, m2H), 1.4–1.5 (s, 3H).

b) 9-methyl-N-[3-(9-(2,7-dichlorofluorenyl)) propionyl]-4-aminobenzoic acid, (2,7-Dichlorofluorenyl)-9-propionic acid (1.40 g, 4.36 mmol), ethyl 4-aminobenzoate (0.72 g, 4.36 mmol), (1-(3dimethylaminopropyl)-3-ethyl)carbodiimide hydrochloride (0.90 g, 4.36 mmol) and N-dimethyl aminopyridine (catalytic amount) was suspended in 20 mL of anhydrous methylene chloride under argon and stirred for 18 hours. The solvent was evaporated and the residue after silica gel column separation using 20% ethyl acetate/hexane as eluent gave 1.86 g (91%) of ester as a white solid. The ester was dissolved in 20 mL of $MeOH:H_2O$ (6:1), mixed with potassium bicarbonate (2.74 g, 20 mol) and refluxed for 6 hours. The methanol was evaporated and acidified with dilute. HCl to get the product as white solid. It was then recrystallized from aqueous methanol to provide 930 mg (53%) of 9-methyl-N-[3-(9-(2,7-dichlorofluorenyl)) propionyl]-4-aminobenzoic acid as a white solid, mp 237° C.–238° C., IR: 3311, 1673, 1602, 1540, 1453, 1409, 1252, 1178, 859, 812, 771. $H^1$ NMR ($CDCl_3$, 300 MHz) d 7.4–8.0 (m, 10H), 2.4–2.5 (t, 2H), 1.5–1.6 (t, 2H), 1.4–1.5 (s, 3H). Anal. Calcd for $C_{24}H_{19}Cl_2NO_3$: C, 65.47; H, 4.34; N, 3.18; Cl, 16.10. Found: C, 65.52; H, 4.34; N, 3.19; Cl, 16.01.

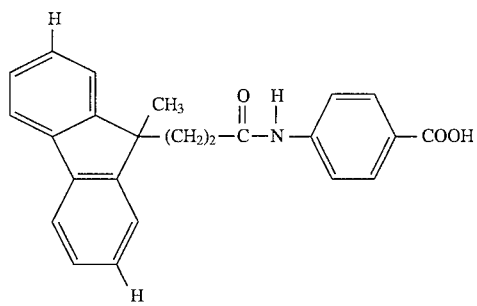

EXAMPLE 22

9-Methyl-N-[3-(9-fluorenyl))propionyl]-4-aminobenzoic acid 3-(9-Fluorenyl]propionic acid. The compound was prepared according to the procedure of Example 21, steps a) and b) and showed $H^1$ NMR ($CDCl_3$, 300 MHz) δ 7.4–8.0 (m, 8H) , 2.3–2.4 (m, 2H) , 1.5–1.6 (m, 2H) , 1.4–1.5 (s, 3H).

9-Methyl-N-[3-(9-fluorenyl))propionyl]-4-aminobenzoic acid. The compound was prepared by the procedure described in step c of Example 21 and produced a white solid having mp 216° C.–217° C. IR: 3404; 1687; 1597; 1532; 1409: 1311; 1280; 1255; 1175; 859; 764; 735. $H^1$ NMR (CDCl$_3$, 300 MHz) δ 7.4–8.0(m, 12H), 1.40–1.50(s, 3H), 2.20–2.40(t, 2H), 1.40–1.60(t, 2H). Anal. Calcd for C$_{24}$H$_{21}$NO$_3$: c, 77.61; H, 5.70;,N, 3.77. Found: C, 77.61; H, 5.70; N, 3.74.

Example 23 demonstrates the formation of compounds by the following scheme (Scheme 4).

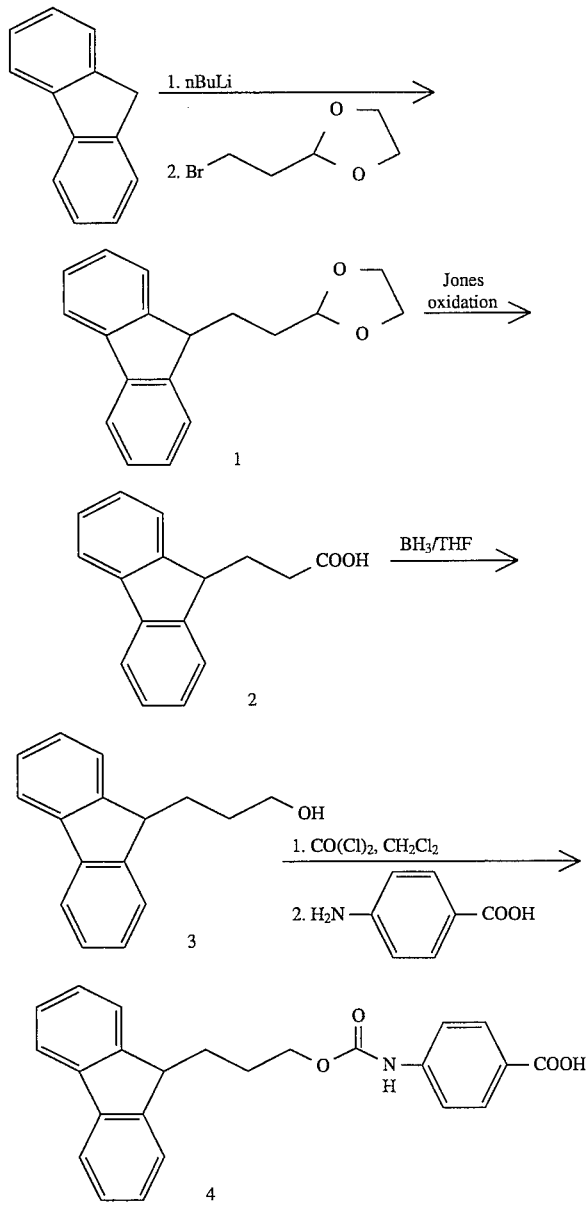

EXAMPLE 23

(4-[3-(9H-Fluoren-9-yl) propoxycarbonyl]-aminobenzoic acid) (4)

2-(2-[9H-Fluorenyl]ethyl)-1,3-dioxolane (1)

A solution of fluorene (5.04 g; 30.32 mmol) in THF (50 mL) was cooled to 0° C. and treated with n-butyllithium (12.13 mL of a 2.5M solution in hexanes; 30.32 mL). After stirring the resulting dark red mixture for 20 minutes, a solution of 2-(2-bromoethyl)-1,3-dioxolane (6.03 g; 33.35 mmol) in 20 mL of THF was added, and the resulting mixture was stirred overnight, allowing it to come to room temperature. It was quenched by the addition of saturated ammonium chloride (50 mL) and extracted into ethyl acetate (50 mL). The organic phase was washed with brine, dried and freed of solvent. The crude residue was purified on a flash chromatography column, eluting with 20% ethyl acetate in hexane, to obtain 5.74 g (72%) of the product as an oil. $^1$H NMR (CDCl$_3$): δ 1.43 (m, 2H); 2.18 (m, 2H); 3.82, 3.86 (m, 2H each); 4.15 (t, 1H); 4.77 (t, 1H); 7.31 (m, 4H); 7.51 (dd, 2H); 7.68 (dd, 2H).

3-(9H-Fluorenyl)-propionic acid (2)

Jones reagent (2.3M) was added dropwise to a solution of 1 (5.69 g; 21.53 mmol) in acetone (100 mL). After stirring for 5 hours the reaction mixture was partitioned between ether (100 mL) and water (100 mL). The layers were separated and the aqueous layer was extracted twice with ether; the combined ether layers were washed with water twice and freed of solvent. The product was obtained as a white solid (4.77 g; 94%), of sufficient purity to use in the subsequent step directly. $^1$H NMR (CDCl$_3$): δ 1.88 (m, 2H); 2.43 (m, 2H); 4.15 (t, 1H); 7.33 (m, 4H); 7.45 (dd, 2H); 7.71 (dd, 2H).

3-(9H-Fluorenyl)-propyl alcohol (3)

A solution of the carboxylic acid material 2 (9.0 g; 37.8 mmol) in THF 200 mL was cooled to 0° C. and treated with a solution of diborane in THF (80 mL of a 1.0M solution; 80 mmol). The mixture was stirred overnight, then quenched with 1N HCl and extracted into ethyl acetate. The organic phase was dried and freed of solvent, and the resulting crude material was purified on a flash column, eluting with 30% ethyl acetate in hexane, to obtain 6.90 g (81%) of the alcohol as an oil. $^1$H NMR (CDCl$_3$): δ 1.34 (m, 2H); 1.71 (m, 1H); 2.16 (m, 2H); 3.52 (m, 2H); 4.06 (m, 1H); 7.34 (m, 4H); 7.54 (d, 2H, J=7.26); 7.78 (d, 2H, J=7.26).

4-[3-(9H-Fluoren-9-yl)propoxycarbonyl]-aminobenzoic acid (4)

A solution of the alcohol material 3 (6.90 g; 30.8 mmol) in a mixture of THF and methylene chloride (300 mL of a 1:1 mixture) was cooled to 0° C. A solution of phosgene in toluene (11.3 mL of a 4.1M solution; 45 mmol) was added and the ice bath was removed. The resulting mixture was stirred at room temperature for 2.5 hours and then concentrated in vacuo to afford the crude chloroformate as an oil. This material was redissolved in THF (100 mL) and added dropwise to a cooled (0° C.) solution of para-aminobenzoic acid (8.51 g; 62 mmol) in THF. After the addition was complete the reaction mixture was stirred overnight. It was partioned between 1N HCl (500 mL) and ethyl acetate (500 mL). The organic phase was washed with 2×500 mL of 1N HCl, dried and concentrated. The crude material was recrystallized from methanol/water to obtain 7.6 g of product as white crystals (64%), mp 205°–207° C. $^1$H NMR (DMSO-d$^6$): δ 1.37 (m, 2H); 2.07 (m, 2H); 4.02 (m, 3H); 7.33 (m, 4H); 7.54 (m, 4H); 7.83 (m, 4H); 9.90 (s, 1H); 12.62 (s, 1H). IR (KBr): 3343, 2949, 2661, 2548, 1707, 1682, 1610, 1592, 1530, 1509, 1414, 1311, 1293, 1227, 1175, 1057, 941, 854, 774, 741 cm$^{-1}$. Anal. Calcd. for C$_{24}$H$_{21}$NO$_4$: C, 74.4; H, 5.46; N, 3.62. Found: C, 74.32; H, 5.49; N, 3.61.

Example 24 demonstrates the formation of compounds by the following scheme (Scheme 5):

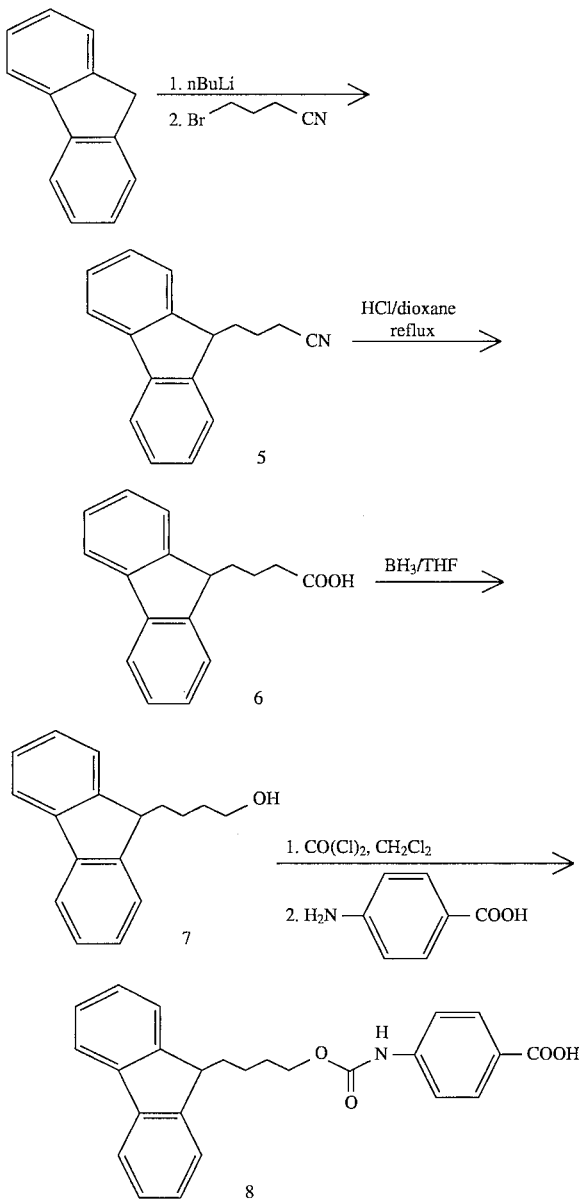

EXAMPLE 24

(4-[4-(9H-Fluoren-9-yl)butoxycarbonylamino]benzoic acid) (8)

4-(9H-Fluoren-9-yl)butyronitrile (5)

A solution of fluorene (5.04 g; 30.32 mmol) in THF (50 mL) was cooled to 0° C. and treated with n-butyllithium (12.13 mL of a 2.5M solution in hexanes; 30.32 mmol). After stirring the red anion mixture for 15 minutes, 4-bromobutyronitrile (4.86 g; 31.84 mmol) in 20 mL of THF was added via syringe, and the mixture was stirred overnight. It was quenched with 100 mL of saturated ammonium chloride and extracted into ethyl acetate (2×75 mL); the organic portions were washed with brine, dried and concentrated. The crude product was purified on a silica gel column, eluted with 20% ethyl acetate in hexane, to afford 4.91 g (70%) of the product as an orange oil. $^1$H NMR (CDCl$_3$): δ 1.38 (m, 4H); 2.18, 2.29 (m, 2H each); 4.10 (m, 1H); 7.37 (m, 4H); 7.45 (d, 2H); 7.75 (d, 2H).

4-(9H-Fluoren-9-yl)butyric acid (6)

To a solution of the nitrile material 5 (20.4 g; 87.44 mmol) in 60 mL of dioxane was added 120 mL of concentrated HCl, and the resulting mixture was brought to reflux for four hours. After cooling, the reaction mixture was extracted with 3×100 mL of ethyl acetate and the ethyl acetate portions were combined and concentrated. The residue was taken up in 200 mL of 1N KOH and washed with 3 portions of ether. The aqueous phase was then made strongly acidic (pH 1) with concentrated HCl and extracted with 3 portions of ethyl acetate. The organic layers were combined, dried, and concentrated to afford 14.20 g (64%) of the acid as a white solid. $^1$H NMR (CDCl$_3$): δ 1.44 (m, 2H); 2.08 (m, 2H); 2.25 (t, 2H); 4.00 (t, 1H); 7.31 (m, 4H); 7.49 (d, 2H, J=7.3); 7.74 (d, 2H, J=7.3).

4-(9H-Fluoren-yl)butyl alcohol (7)

A solution of the acid material 6 (3.50 g; 13.90 mmol) in 30 mL of THF was cooled to 0° C. and treated with 13.90 mL of a 1.0M solution of borane in THF (13.90 mmol). The resulting mixture was stirred overnight, then quenched with saturated ammonium chloride (30 mL). The product was extracted into ethyl acetate, and the organic phase was washed successively with 3% HCl, saturated sodium bicarbonate, and brine. Removal of the solvent furnished the alcohol (2.90 g; 88%), which crystallized to a waxy solid on standing and did not require further purification. $^1$H NMR (CDCl$_3$): δ 1.22 (m, 2H); 1.49 (m, 2H); 1.98 (m, 2H); 3.50 (t, 2H); 3.95 (t, 1H); 7.33 (m, 4H); 7.49 (d, 2H, J=7.3); 7.73 (d, 2H, J=7.3).

4-[4-(9H-Fluoren-9-yl)butoxycarbonylamino]benzoic acid (8)

A solution of the alcohol material 7 (1.0 g; 4.2 mmol) in 40 mL of a 1:1 mixture of methylene chloride:THF was treated with 1.4 mL of a 4.2M solution of phosgene in methylene chloride (5.90 mmol). The resulting mixture was stirred for one hour and then concentrated in vacuo. The residue was redissolved in 30 mL of methylene chloride and added to a solution of para-amino benzoic acid (1.15 g; 8.4 mmol) in 20 mL of CH$_2$Cl$_2$. The mixture was stirred overnight and then concentrated. The residue was partitioned between ethyl acetate and 10% HCl. The organic phase was washed with brine, dried and concentrated. The crude product was recrystallized from ether/hexane to obtain 0.60 g (35%) as a white solid, mp 146°–149° C. $^1$H NMR (DMSO-d6): δ 1.20 (m, 2H); 1.61 (m, 2H); 2.10 (m, 2H); 4.06 (m, 3H); 7.37 (m, 8H); 7.75 (d, 2H); 8.05 (d, 2H). IR (KBr); 3325, 3065, 2932, 2862, 2669, 2551, 1697, 1684, 1607, 1527, 1448, 1414, 1314 cm$^{-1}$. Anal. Calcd. for C$_{25}$H$_{23}$NO$_4$-0.25 H$_2$O: C, 73.96; H, 5.83; N, 3.45. Found: C, 73.72; H, 5.87; N, 3.45.

Example 25 demonstrates the formation of compounds by the following scheme:

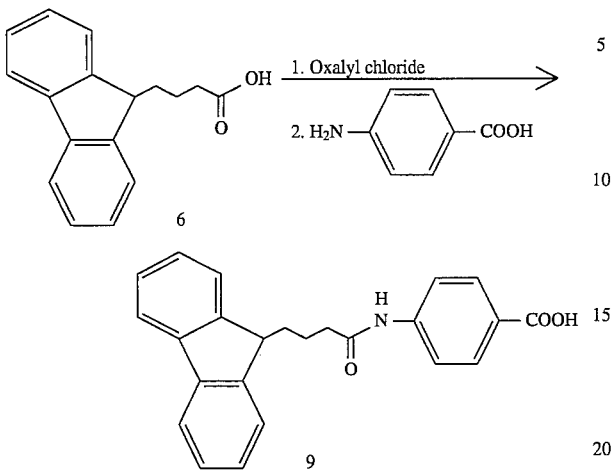

EXAMPLE 25

(4-[9H-(Fluoren-9-yl)]butyric acid-4-carboxyanilide) (9)

A mixture of the carboxylic acid material of Scheme 5 identified as 6 (3.50 g; 13.87 mmol) and oxalyl chloride (20 mL) was treated with 2 drops of dimethylformamide. The resulting mixture was stirred for 2 hours at room temperature and then evaporated to dryness under reduced pressure to furnish the crude acid chloride. This was dissolved in 60 mL of a 1:2 mixture of 10% aqueous potassium carbonate and dioxane and para-amino benzoic acid (3.80 g; 27.6 mmol) was added. This mixture was stirred overnight and then concentrated to dryness. The residue was taken up in ethyl acetate and washed 5 times with 1N HCl. The organic phase was dried and evaporated, and the crude product was recrystallized from ethyl acetate:hexane to obtain 1.60 g (31%) of 9; $^1$H NMR (DMSO-d6): δ 1.35 (m, 2H); 2.03 (m, 2H); 2.29 (t, 2H); 4.03 (t, 1H); 7.34 (m, 4H); 7.60 (m, 4H); 7.84 (m, 4H); 10.13 (s, 1H); 12.66 (s, 1H). IR (KBr): 3271, 3023, 2621, 2543, 1669, 1670, 1594, 1525, 1448, 1422, 1309, 1286, 1255, 1175 cm$^{-1}$. Anal. Calcd. for $C_{24}H_{21}NO_3$: C, 77.61; H, 5.70; N, 3.77. Found: C, 77.46; H, 5.76; N, 3.73.

Example 26 demonstrates the formation of compounds by the following scheme (Scheme 7):

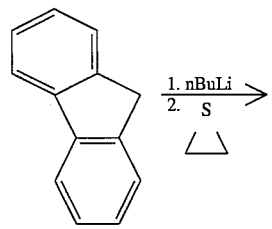

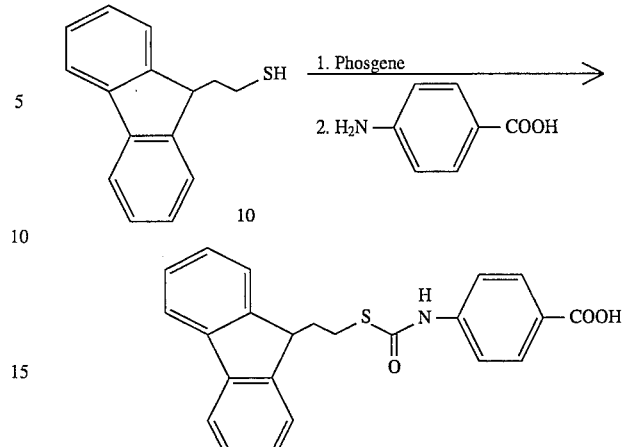

EXAMPLE 26

(N-[2-(9H-Fluoren-9-yl)ethylthioxycarbonyl-4-aminobenzoic acid) (11)

9H-Fluorene-9-ethanethiol (10)

A solution of fluorene (20.0 g; 120 mmol) in THF (200 mL) was cooled to −40° C. and treated with 48 mL of a 2.5M solution of n-butyllithium in hexanes (120 mmol). After stirring for 15 minutes, a solution of ethylene sulfide (6.5 mL; 109 mmol) in 30 mL of THF was added, and the resulting mixture was stirred at −40° C. for 30 minutes and room temperature for 2 hours. The reaction was quenched by the addition of saturated ammonium chloride, the layers were separated, and the organic phase was washed with 10% HCl, dried and concentrated. The crude product was purified on a flash column, eluting with hexane, to provide 16.8 g (62%) of the product as an oil that recrystallized from hexane as a white solid, mp 38°–40° C.

N-[2-(9H-Fluoren-9-yl)ethylthioxycarbonyl]-4-aminobenzoic acid (11)

A solution of the thiol material 10 (3.0 g; 13.2 mmol) in methylene chloride (30 mL) was treated with 8.5 mL of a 1.93M solution of phosgene in toluene (16.4 mmol). After stirring for 1 hour the mixture was concentrated under reduced pressure, redissolved in 25 mL of dioxane, and added dropwise to a stirred mixture of potassium carbonate (2.26 g 16.4 mmol) and paraaminobenzoic acid (1.80 g; 13.2 mmol) in 20 mL of water. After stirring overnight, the layers were separated and the aqueous layer was extracted with 2×15 mL of ethyl acetate. The aqueous layer was cooled and acidified to pH 1 with 6N HCl; the formed precipitate was collected and washed with cold methanol and dried under vacuum. Thiocarbamate 11 was obtained as a white solid (3.40 g; 69%). $^1$H NMR (DMSO-d6): δ 2.28–2.35 (m, 2H); 2.62–2.70 (m, 2H); 4.08–4.12 (m, 1H); 7.33–7.43 (m, 4H); 7.53–7.65 (m, 4H); 7.82–7.90 (m, 4H). IR (KBr): 3332, 3020, 1676, 1607, 1517, 1409, 1295, 1244, 1149, 736 cm$^{-1}$. Anal. Calcd. for $C_{23}H_{19}NO_3S$, C 70.93; H, 4.92; N, 3.60; S, 8.23. Found: C, 70.67; H, 4.88; N, 3.84; N, 8.08.

Examples 27 and 28 demonstrate the formation of compounds by the following scheme (Scheme 8) wherein X is chlorine in Example 27 and bromine in Example 28.

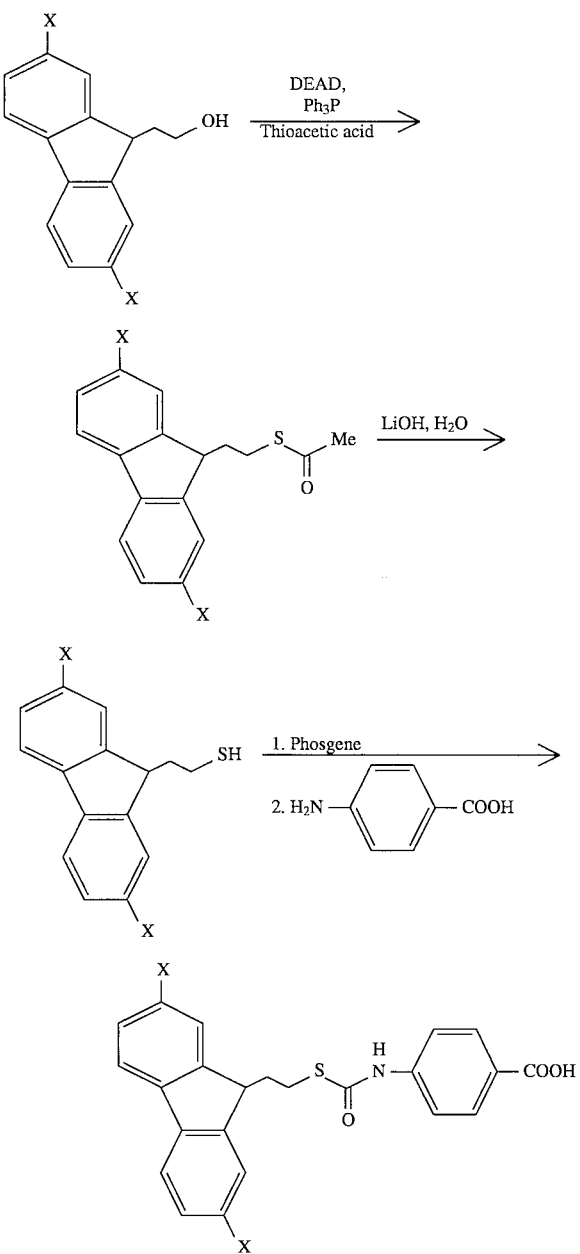

EXAMPLES 27 AND 28

(N-[9H-(2,7-Dichlorofluoren-9-ylthioethoxy carbonyl)]-4-aminobenzoic acid) (18) and (N-[9H-(2,7-dibromofluoren-9-ylthioxycarbonyl)]-4-amino benzoic acid) (19)

The alcohol material 12 (7.88 g; 28.22 mmol) and triphenylphosphine oxide (9.00 g; 33.97 mmol) were dissolved in 100 mL of THF and cooled to −78° C. Diethyl azidodicarboxylate (5.4 mL; 34.29 mmol) in 20 mL of THF was added and the mixture was stirred for 10 minutes, at which point thioacetic acid (2.2 mL; 29.55 mmol) in 15 mL of THF was added. The cooling bath was removed and the mixture was stirred at room temperature overnight. The volatiles were removed under reduced pressure and the residue was purified on a silica gel column, eluting with 2% ethyl acetate in hexane, to obtain 7.30 g (77%) of the thioester as an oil. $^1$H NMR (CDCl$_3$): δ 2.24–2.30 (m, 5H); 2.61–2.78 (m, 2H); 4.04 (t, 1H); 7.36 (dd, 2H); 7.51 (s, 2H); 7.62 (d, 2H).

Repetition of the above procedure using the dibromo compound 13 furnished the corresponding thioester 15 in 88% yield; $^1$H NMR (CDCl$_3$): δ 2.24–2.29 (m, 2H); 2.31 (s, 3H); 2.62–2.67 (m, 2H); 4.05 (t, 1H); 7.51 (dd, 2H); 7.58 (d, 2H); 7.67 (s, 2H).

2,7-Dichloro-9-fluorenylethanethiol (16)

Concentrated sulfuric acid (1.7 mL) was added to a suspension of thioester 14 (7.00 g; 20.76 mmol) in 55 mL of methanol and the resulting mixture was refluxed for 3 hours. The solid which formed upon cooling was filtered off to obtain 4.70 g (77%) of pure thiol, mp 96°–97° C. $^1$H NMR (CDCl$_3$): δ 1.34–1.38 (m, 1H); 2.27–2.84 (m, 4H); 4.11 (broad s, 1H); 7.34–7.37 (m, 2H); 7.46–7.47 (m, 2H); 7.62 (d, 2H).

Starting with thioester 15, thiol 17 was obtained in 87% yield. $^1$H NMR (CDCl$_3$): δ 1.34–1.38 (m, 1H); 2.29–2.32 (m, 4H); 4.11 (br s, 1H); 7.51 (dd, 2H); 7.58 (d, 2H); 7.62 (s, 2H).

N-[9H-(2,7-Dichlorofluoren-9-ylthioethoxycarbonyl)]-4-aminobenzoic acid (18)

The reaction of the thiol material 16 with, successively, phosgene and para-aminobenzoic acid was carried out as described above. The thiocarbamate 18 was obtained in 73% yield, mp 243°–245° C. $^1$H NMR (DMSO-d6): δ 2.34–2.40 (m, 2H); 2.55–2.60 (m, 2H); 4.19 (t, 1H); 7.45 (d, 1H); 7.47 (d, 1H); 7.56 (d, 2H); 7.73 (s, 2H); 7.85 (d, 2H); 7.92 (d, 2H). IR (KBr): 3286, 3260, 3188–2864, 2661, 2545, 1681, 1597, 1532, 1421, 1409, 1309, 1296, 1250, 1165 cm$^{-1}$. Anal. Calcd. for C$_{23}$H$_{17}$Cl$_2$NO$_3$S: C, 60.27; H, 3.74; N, 3.06; S, 6.99; Cl, 15.47. Found: C, 60.38; H, 3.93; N, 3.02; S, 7.04: Cl, 15.36.

N-[9H-(2,7-Dibromofluoren-9-ylthioethoxycarbonyl)]-4-aminobenzoic acid (19)

The thiocarbonate 19 was obtained in 84% yield, mp 236°–240° C. $^1$H NMR (CDCl$_3$): δ 2.34–2.39 (m, 2H); 2.55–2.59 (m, 2H); 4.19 (t, 1H); 7.55–7.61 (m, 4H); 7.84–7.88 (m, 6H). IR (KBr): 3289, 3140–2859, 2548, 1679, 1656, 1597, 1530, 1409, 1309, 1291, 1247, 1162 cm$^{-1}$. Anal. Calcd. for C$_{23}$H$_{17}$Br$_2$NO$_3$S: C, 50.48; H, 3.13; N, 2.56; S, 5.86; Br, 29.20. Found: C, 50.52; H, 3.09; N, 2.62; S, 5.83; Br, 29.28.

EXAMPLE 29

Male Sprague Dawley rats, 150–200 g, were anesthetized with isoflurane. The drug from Example 7, namely N-[9H-(fluorenyl-9-ethoxycarbonyl)amino-4-benzoic acid was administered intraperitoneally in 0.5% methylcellulose or water at three doses, 10 mg/kg, 30 mg/kg, 100 mg/kg. The rat was then injected intradermally in the distal third of the tail with 0.1 ml of saline or 0.1 ml of well-sonicated squalene containing 1 mg/ml *Mycobacterium tuberculosis*. Rats were then returned to their cages. On days 1 and 2 after the adjuvant injection, each rat was weighed and dosed with vehicle or drug suspension as before, but without anesthesia. On day 3, each rat was weighed and anesthetized with sodium pentobarbital. Blood was drawn by cardiac puncture into 0.2 ml of EDTA solution (12 mg/ml). Blood samples were centrifuged and the plasma was removed. The fibrinogen was converted into fibrin using sodium sulfite and the resulting fibrin was assayed using a Lowry protein assay to estimate initial fibrinogen levels. Percent inhibition by test compound was determined by substracting fibrinogen level in non-Freund's adjuvant-injected rats from fibrinogen levels in rats injected with adjuvant alone and those rats injected with adjuvant plus test compound, and inhibited to a maximum of 50%, achieved at a dose of 3 mg/kg when the drug was given orally. Basal plasma fibrinogen levels were elevated from 2.44±0.08 mg/ml to 8.6±0.2 mg/ml (n=25), in different experiments. The drug by itself elevated plasma fibrinogen levels to 4.8±0.6 at 100 mg/kg (p.o.) (n=5).

When the test was repeated with the compound of Example 14, namely N-[3-(9-Fluorenyl)propionyl]anthranilic acid at doses of 10, 30, and 100 mg/kg plasma fibrinogen levels .were inhibited 22%, 19%, and 51%, respectfully.

EXAMPLE 30

The adjuvant arthritis test of Example 29 was repeated at doses ranging from 0.3 to 100 mg/kg administered intraperitoneally and orally with compounds produced in Examples 7, 8, 9, 25, 26, 27, and 28. The results are set forth in Table 1.

TABLE I

| Example | AA * (i.p.)<br>% inhibition at<br>100 mg/kg | AA * (p.o.)<br>% inhibition at<br>100 mg/kg |
| --- | --- | --- |
| 7 | 63% | 39% |
| 8 | 69% | 48% |
| 9 | 78% | 38% |
| 25 | — | 15% |
| 26 | 70% | 56% |
| 27 | 54% | 52% |
| 28 | 72% | 41% |

* Inhibited plasma fibrinogen in arthritis model.

EXAMPLE 31

Reverse Passive Arthus Reaction (RPA)

Male SD rats weighing between 200 and 300 g were used. Test compounds were dissolved in dimethyl sulfoxide and 1 ml/kg of this stock solution (100 mg/ml), on serial dilutions were injected intraperitoneally one hour before administration of the antigen or given orally. The animals were anesthetized inhalationally with isoflurane and then injected through the penile vein with 1 ml of a solution of 2.5 mg of Evan's blue dye and 5.0 mg of human serum albumin in 1 ml of saline. This treatment was followed immediately by intracutaneous injections of 0.075 ml of anti-human albumin diluted to contain 4.38 mg/ml of antibody at 2 sites opposite the midline back. Anesthesia was terminated and after three hours, the animals were sacrificed. The skin was removed and the blue stained areas cut out. The skin patches were soaked overnight in stoppered tubes containing 2 ml of 1N potassium hydroxide at 5° C. Then 9 ml of a mixture of five parts of a 1.2N phosphoric acid and thirteen parts of acetone were added to the tubes. The tube contents were agitated and centrifuged, and the absorbance measured at 620 nm. The data were calculated as inhibition of blueing by test compound compared to control animals receiving only antigen and antibody. The RPA inhibition results are reported in Table II.

TABLE II

| Example | RPA (i.p.)<br>$ED_{50}$ | RPA (p.o.)<br>100 mg/kg |
| --- | --- | --- |
| 7 | 70 mg/kg | 25% |
| 8 | 100 mg/kg | 0% |
| 9 | 34 mg/kg | 54% |
| 25 | not done | 0% |
| 23 | not done | 1% |
| 28 | not done | 1% |

EXAMPLE 32

Inhibition of Ear Edema Caused by Oxazolone

CF-1 mice, 25–30 g body weight, six animals per group were used. The mice were sensitized to the irritant two weeks prior to the test by dribbling 100 μL of a 3% solution of oxazolone in acetone onto the scrotum of the animal. Test compounds were administered orally at doses of 100 mg/kg and 300 mg/kg for 1 hour prior to oxazolone, intraperitoneally as follows: The test compound was dissolved in dimethyl sulfoxide and doses of 10 mg/kg, 30 mg/kg, and 100 mg/kg were injected 15 mintures prior to irritant. The irritant, 3% oxazolone in acetone, was added to the surface of the ear, 5 μL added to the upper surface and 5 μL added to the lower surface. After twenty four hours the thickness of the ear was measured to 0.01 mm by a micrometer with loose drag, positioned at the lateral-most edge of the midpoint of the pinna. Data were calculated as the inhibition of increased ear thickness compared to control animals' receiving only the irritant. In general, % inhibition of greater than 20% is statistically significant ($p<0.05$ or less, Student's t-test for unpaired data).

The results indicated that oxazolone increased ear thickness from a value of 0.3 mm to 0.6 mm. The drug from Example 7 inhibited this response in a dose-dependent manner by 46%, 82%, and 79%, at doses of 10, 30, ad 100 mg/kg, respectfully, when given i.p., and by 50% when given orally.

EXAMPLE 33

Determination of Myeloperoxidase (MPO) Activity

Colonic tissues were assessed biochemically by the activity of the neutrophil marker enzyme, MPO. Approximately 50 mg of mucosal scrapings were homogenized (30 sec, 4° C.) in 1 ml of 0.5% hexadecyltrimethylammonium bromide detergent. The homogentate was then sonicated (10 sec), subjected to three freeze thaw cycles, and centrifuged (15 min, 40,000 g). MPO was assayed spectrophotometrically by determining the decomposition of peroxide using o-dianisidine as the hydrogen donor. Data was expressed as the mean absorbance (460 nm) ±S.E.M. at 15 min, per gram wet weight.

The drug of Examples 7 and 9 were tested orally for their ability to inhibit acetic acid induced colonic inflammation as measured by myeloperoxidose activity (MPO) and/or by dye extravasation, at doses ranging from 1 mg/kg to 100 mg/kg. Acetic acid caused a 25-fold increase in MPO activity.

The invention being thus described, it will be obvious that the same may be varied in many ways. Such variations are not to be regarded as a departure from the spirit and scope of the invention and all such modifications are intended to be included within the scope of the following claims.

What is claimed:
1. A compound having the formula:

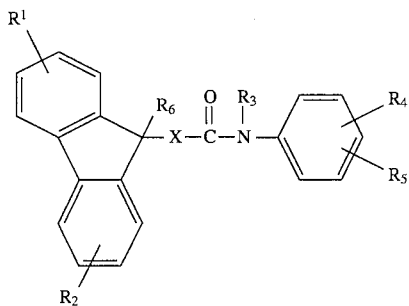

wherein:
- X is selected from the group consisting of $(CH_2)_n$, $(CH_2)_nO$ wherein n is 3 to 11, and $(CH_2)_{m-1}S$ wherein m is 1 to 11 and wherein the chains are straight or branched chain;
- $R_1$ and $R_2$ are independently selected from the group consisting of hydrogen, $C_1$ to $C_6$ straight or branched chain lower alkyl, aryl, aralkyl, alkoxy, alkoxyalkyl, halogen, nitro and mixtures thereof;
- $R_3$ is selected from the group consisting of hydrogen and $C_1$ to $C_6$ straight or branched chain lower alkyl groups;
- $R_4$ is selected from the group consisting of —$CO_2H$; —$NHSO_2R_7$, wherein $R_7$ is methyl, or trifluoromethyl; —$CONHSO_2R_8$, wherein $R_8$ is methyl, trifluoromethyl, or phenyl; 1H-tetrazol-5-yl; —$(CH_3)_nCOOH$ wherein n is 1, 2 or 3; and —CONH-tetrazol-5-yl;
- $R_5$ is selected from the group consisting of hydrogen, $C_1$ to $C_4$ straight or branched chain lower alkyl, halogen, hydroxyl, and a methoxy group; and
- $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic hydrocarbo groups.

2. The compound of claim 1, wherein X is selected from the group consisting of propyleneoxy, butyleneoxy, propylene and thioethylene.

3. The compound of claim 1, wherein $R_1$, and $R_2$ are independent selected from the group consisting of hydrogen, chlorine, bromine, and mixtures thereof.

4. The compound of claim 1, wherein $R_1$ and $R_2$ are selected from the group consisting of 2,7-dimethyl, 2,7-diethyl, 2,7-di-t-butyl, 2,7-dibromo, and 2,7-dichloro.

5. The compound of claim 1, wherein $R_4$ is selected from the group consisting of -2—$CO_2H$, -3—$CO_2H$, -4—$CO_4H$, and -4—$CH_2CO_2H$.

6. The compound of claim 1, wherein $R_5$ is selected from the group consisting of hydrogen, hydroxyl, and methyl group.

7. The compound of claim 1, selected from the group consisting of:
- (4-[3-(9H-Fluoren-9-yl) propoxycarbonyl]-aminobenzoic acid);
- (4-[4-(9H-Fluoren-9-yl) butoxycarbonylamino]benzoic acid);
- (4-[9H-Fluoren-9-yl)]butyricacid-4-carboxyanilide);
- (N-[2-(9H-Fluoren-9-yl)ethylthioxycarbonyl]-4-aminobenzoic acid);
- (N-[9H-(2,7-Dichlorofluoren-9-ylthioethoxycarbonyl)]-4-aminobenzoic acid); and
- (N-[9H-(2,7-dibromofluoren-9-ylthioxycarbonyl)]-4-aminobenzoic acid).

8. A method of treating an inflammatory condition comprising administering to an animal in need of such treatment an amount of at least one compound represented by the following formula:

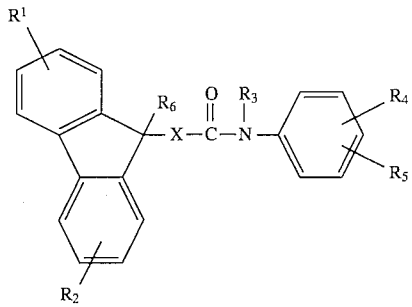

wherein:
- X is selected from the group consisting of $(CH_2)_n$, $(CH_2)_nO$ wherein n is 3 to 11, and $(CH_2)_{m-1}S$ wherein m is 1 to 11 and wherein the chains are straight or branched chain;
- $R_1$ and $R_2$ are independently selected from the group consisting of hydrogen, $C_1$ to $C_6$ straight or branched chain lower alkyl, aryl, aralkyl, alkoxy, alkoxyalkyl, halogen, nitro and mixtures thereof;
- $R_2$ is selected from the group consisting of hydrogen and $C_1$ to $C_6$ straight or branched chain lower alkyl groups;
- $R_4$ is selected from the group consisting of —$CO_2H$; —$NHSO_2R_7$, wherein $R_7$ is methyl, or trifluoromethyl; —$CONHSO_2R_8$, wherein $R_8$ is methyl, trifluoromethyl, or phenyl; 1H-tetrazol-5-yl; —$(CH_2)_nCOOH$, wherein n is 1, 2 or 3; and —CONH-tetrazol-5yl;
- $R_6$ is selected from the group consisting of hydrogen, $C_1$ to $C_4$ straight or branched chain lower alkyl, halogen, hydroxyl, and a methoxy groups; and
- $R_4$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic hydrocarbo groups.

9. The method of claim 8, wherein X is selected from the group consisting of propyleneoxy, butyleneoxy, propylene, and thioethylene.

10. The method of claim 8, wherein $R_1$, and $R_2$ are independently selected from the group consisting of hydrogen, chlorine, bromine, and mixtures thereof.

11. The method of claim 8, wherein $R_1$ and $R_2$ are selected from the group consisting of 2,7-dimethyl, 2,7-diethyl, 2,7-di-t-butyl, 2,7-dibromo, and 2,7-dichloro.

12. The method of claim 8, wherein $R_4$ is selected from the group consisting of -2—$CO_2H$, -3—$CO_2H$, -4—$CO_2H$, and -4—$CH_2$—$CO_2H$.

13. The method of claim 8, wherein $R_5$ is selected from the group consisting of hydrogen, hydroxyl, and a methyl group.

14. The method of claim 8, selected from the group consisting of:
- (4-[3-(9H-Fluoren-9-yl)propoxycarbonyl]-aminobenzoic acid);
- (4-[4-(9H-Fluoren-9-yl)butoxycarbonylamino]benzoic acid);
- (4-[9H-Fluoren-9-yl)]butyric acid-4-carboxyanilide);

(N-[2-(9H-Fluoren-9-yl)ethylthioxycarbonyl]-4-aminobenzoic acid);

(N-[9H-(2,7-Dichlorofluoren-9-ylthioethoxycarbonyl)]-aminobenzoic acid); and (N-[9H-(2,7-dibromofluoren-9-ylthioxycarbonyl)]-4-aminobenzoic acid).

15. A pharmaceutical composition suitable for use in producing an anti-inflammatory effect in an animal comprising, as an effective ingredient, an amount of at least one compound of the following formula administered to an animal together with a pharmaceutically acceptable carrier or diluent

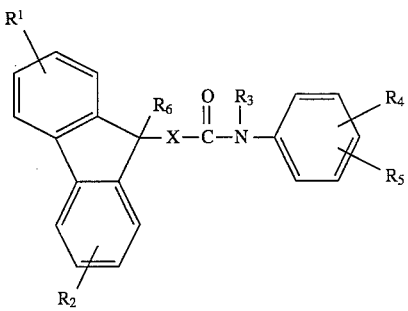

wherein:
X is selected from the group consisting of $(CH_2)_n$, $(CH_2)_nO$ wherein n is 3 to 11, and $(CH_2)_{n-1}S$ wherein m is 1 to 11, and wherein the chains are straight or branched chain;

$R_1$ and $R_2$ are independently selected from the group consisting of hydrogen, $C_1$ to $C_6$ straight or branched chain lower alkyl, aryl, aralkyl, alkoxy, alkoxyalkyl, halogen, nitro and mixtures thereof;

$R_3$ is selected from the group consisting of hydrogen and $C_1$ to $C_6$ straight or branched chain lower alkyl groups;

$R_4$ is selected from the group consisting of —$CO_2H$; —$NHSO_2R_7$, wherein $R_7$ is methyl, or trifluoromethyl; —$CONHSO_2R_8$, wherein $R_8$ is methyl, trifluoromethyl, or phenyl; 1H-tetrazol-5-yl; —$(CH_2)_nCOOH$, wherein n is 1, 2 or 3; and —CONH-tetrazol-5-yl;

$R_8$ is selected from the group consisting of hydrogen, $C_1$ to $C_6$ straight or branched chain lower alkyl, halogen, hydroxyl, and a methoxy group; and $R_6$ is selected from the group consisting of hydrogen, halogen, $C_1$ to $C_6$ straight or branched chain lower alkyl, $C_1$ to $C_6$ straight or branched chain lower alkoxy, $C_1$ to $C_6$ straight or branched chain lower alkoxy ethers, and alicyclic hydrocarbo groups.

16. The pharmaceutical composition of claim 15, wherein X is selected from the group consisting of propyleneoxy, butyleneoxy, propylene, and thioethylene.

17. The pharmaceutical composition of claim 15, wherein $R_1$, and $R_2$ are independently selected from the group consisting of hydrogen, chlorine, bromine, and mixtures thereof.

18. The pharmaceutical composition of claim 15, wherein $R_1$ and $R_2$ are selected from the group consisting of 2,7-dimethyl, 2,7-diethyl 2,7-di-t-butyl, 2,7-dibromo, and 2,7-dichloro.

19. The pharmaceutical composition of claim 15, wherein $R_4$ is selected from the group consisting of -2—$CO_2H$, -3—$CO_2H$, and 4—$CH_2CO_2H$.

20. The pharmaceutical composition of claim 15, wherein $R_5$ is selected from the group consisting of hydrogen, hydroxyl, and a methyl group.

21. The pharmaceutical composition of claim 15, selected from the group consisting of:

(4-[3-(9H-Fluoren-9-yl) propoxycarbonyl]aminobenzoic acid);

(4-[4-(9H-Fluoren-9-yl) butoxycarbonylamino]benzoic acid);

(4-[9H-Fluoren-9-yl)]butyricacid-4-carboxyanilide);

(N-[2-(9H-Fluoren-9-yl)ethylthioxycarbonyl]-4-aminobenzoic acid);

(N-[9H-(2,7-Dichlorofluoren-9-ylthioethoxycarbonyl)]-4-aminobenzoic acid); and (N-[9H-(2,7-dibromofluoren-9-ylthioxycarbonyl)]-4-aminobenzoic acid).

22. The pharmaceutical composition of claim 15 which is administered orally.

23. The pharmaceutical composition of claim 15 which is administered, parenterally, rectally or topically.

24. The pharmaceutical composition of claim 15 in the form of a powder, lotion, gel, ointment, cream, or sterile aqueous solution.

25. The pharmaceutical composition of claim 15 which is administered transdermally.

* * * * *

UNITED STATES PATENT AND TRADEMARK OFFICE
CERTIFICATE OF CORRECTION

PATENT NO. : 5,519,043
DATED : May 21, 1996
INVENTOR(S) : John J. PERUMATTAM

It is certified that error appears in the above-indentified patent and that said Letters Patent is hereby corrected as shown below:

Column 31,
  line 4, the portion of the formula reading "R$^1$" should read -- R$_1$ --;
  line 34, "C$_4$" should read -- C$_6$ --.

Column 32,
  line 8, the portion of the formula reading "R$^1$" should read -- R$_1$ --;
  line 30, "R$_2$" should read -- R$_3$ --;
  line 36, "-CONH-tetrazol-5yl" should read -- -CONH-tetrazol-5-yl --;
  line 37, "R$_6$" should read -- R$_5$ --;
  line 38, "C$_4$" should read -- C$_6$ --;
  line 39, "groups" should read -- group --;
  line 40, "R$_4$" should read -- R$_6$ --.

Column 33,
  line 4, before "aminobenzoic", -- 4- -- should be inserted;
  line 44, "R$_8$" should read -- R$_5$ --.

Signed and Sealed this

Thirteenth Day of August, 1996

Attest:

BRUCE LEHMAN

Attesting Officer  Commissioner of Patents and Trademarks